(12) United States Patent
Yoshioka et al.

(10) Patent No.: US 9,213,015 B2
(45) Date of Patent: Dec. 15, 2015

(54) BIOLOGICAL SAMPLE MEASURING DEVICE

(75) Inventors: Eriko Yoshioka, Ehime (JP); Teppei Shinno, Ehime (JP); Shouko Hironaka, Ehime (JP)

(73) Assignee: PANASONIC HEALTHCARE HOLDINGS CO., LTD., Minato-Ku, Tokyo ( * ) Notice: Subject to any disclaimer, the term of this patent is extended or adjusted under 35 U.S.C. 154(b) by 314 days.

(21) Appl. No.: 13/982,747

(22) PCT Filed: Feb. 20, 2012

(86) PCT No.: PCT/JP2012/001096
§ 371 (c)(1),
(2), (4) Date: Jul. 30, 2013

(87) PCT Pub. No.: WO2012/114706
PCT Pub. Date: Aug. 30, 2012

(65) Prior Publication Data
US 2013/0306474 A1 Nov. 21, 2013

(30) Foreign Application Priority Data
Feb. 23, 2011 (JP) .................................. 2011-036647

(51) Int. Cl.
*G01N 27/327* (2006.01)
*G01N 27/416* (2006.01)
(Continued)

(52) U.S. Cl.
CPC ................ *G01N 27/416* (2013.01); *A61B 5/05* (2013.01); *C12M 1/34* (2013.01); *C12Q 1/00* (2013.01);
(Continued)

(58) Field of Classification Search
None
See application file for complete search history.

(56) References Cited

U.S. PATENT DOCUMENTS 7,122,110 B2 10/2006 Deng et al.
7,132,041 B2 11/2006 Deng et al.
(Continued)

FOREIGN PATENT DOCUMENTS

CN 1461410 A 12/2003
CN 101354391 A 1/2009
(Continued)

OTHER PUBLICATIONS

International Search Report of PCT Application No. PCT/JP2012/001096.
(Continued)

*Primary Examiner* — Jennifer Dieterle
(74) *Attorney, Agent, or Firm* — Shinjyu Global IP

(57) ABSTRACT

A biological sample measuring device in which a deposited biological sample is introduced into a capillary, a biological sample measuring sensor in which a reagent and the biological sample provided is mounted, and the biological sample is measured. The biological sample measuring device comprises a mounting portion, a voltage application section, and a detection component. The biological sample measuring sensor is mounted to the mounting portion. The voltage application section applies a measurement voltage to a plurality of electrodes disposed along the capillary. The detection component eliminates the effect of seepage of the biological sample by pass-around at the end of the capillary, or the effect whereby the plasma component seeps into the reagent, and detects the degree to which the biological sample is introduced into the capillary, based on the output result for the voltage applied by the voltage application section to the electrodes.

16 Claims, 18 Drawing Sheets

(51) Int. Cl.

| | | |
|---|---|---|
| *G01N 33/49* | (2006.01) | |
| *C12Q 1/00* | (2006.01) | |
| *A61B 5/05* | (2006.01) | |
| *C12M 1/34* | (2006.01) | |
| *G01N 27/417* | (2006.01) | |
| *H01J 49/00* | (2006.01) | |
| *G06K 9/00* | (2006.01) | |
| *G06F 19/24* | (2011.01) | |

(52) U.S. Cl.
CPC ........ *G01N 27/3271* (2013.01); *G01N 27/4175* (2013.01); *G01N 33/49* (2013.01); *G06F 19/24* (2013.01); *G06K 9/00496* (2013.01); *H01J 49/0036* (2013.01)

(56) References Cited

U.S. PATENT DOCUMENTS

| | | | |
|---|---|---|---|
| 7,351,323 B2 | 4/2008 | Iketaki et al. | |
| 7,452,457 B2 | 11/2008 | Burke et al. | |
| 7,547,382 B2 | 6/2009 | Harding et al. | |
| 7,955,492 B2 * | 6/2011 | Fujiwara et al. | 205/777.5 |
| 8,475,638 B2 | 7/2013 | Tokunaga et al. | |
| 8,663,442 B2 | 3/2014 | Burke et al. | |
| 2002/0175075 A1 | 11/2002 | Deng et al. | |
| 2003/0175946 A1 | 9/2003 | Tokunaga et al. | |
| 2004/0154932 A1 | 8/2004 | Deng et al. | |
| 2004/0157337 A1 | 8/2004 | Burke et al. | |
| 2004/0157338 A1 | 8/2004 | Burke et al. | |
| 2004/0157339 A1 | 8/2004 | Burke et al. | |
| 2004/0256248 A1 | 12/2004 | Burke et al. | |
| 2004/0259180 A1 | 12/2004 | Burke et al. | |
| 2004/0260511 A1 | 12/2004 | Burke et al. | |
| 2005/0258034 A1 | 11/2005 | Iketaki et al. | |
| 2006/0037870 A1 | 2/2006 | Deng et al. | |
| 2006/0231418 A1 | 10/2006 | Harding et al. | |
| 2009/0045076 A1 | 2/2009 | Burke et al. | |
| 2010/0258438 A1 | 10/2010 | Tokunaga et al. | |
| 2011/0027816 A1 * | 2/2011 | Fujiwara | 435/25 |
| 2011/0108440 A1 * | 5/2011 | Wu et al. | 205/792 |
| 2011/0144915 A1 * | 6/2011 | Rodgers et al. | 702/19 |
| 2011/0272294 A1 * | 11/2011 | Fujiwara | 205/782 |

FOREIGN PATENT DOCUMENTS

| | | |
|---|---|---|
| EP | 1281955 A1 | 2/2013 |
| JP | 2003-004691 A | 1/2003 |
| JP | 2004-245836 A | 9/2004 |
| JP | 2007-524826 A | 8/2007 |
| JP | 2008-536139 A | 9/2008 |
| JP | 2010-164583 A | 7/2010 |
| JP | 2010-164584 A | 7/2010 |
| WO | WO-02/057768 A1 | 7/2002 |
| WO | WO-02/086483 A1 | 10/2002 |
| WO | 2005/008231 A1 | 1/2005 |

OTHER PUBLICATIONS

The Office Action from the corresponding Chinese Patent Application No. 201280006577.2 issued on Jun. 27, 2014.
The Office Action from the corresponding Japanese Patent Application No. 2013-500879 issued on Aug. 12, 2014.

* cited by examiner

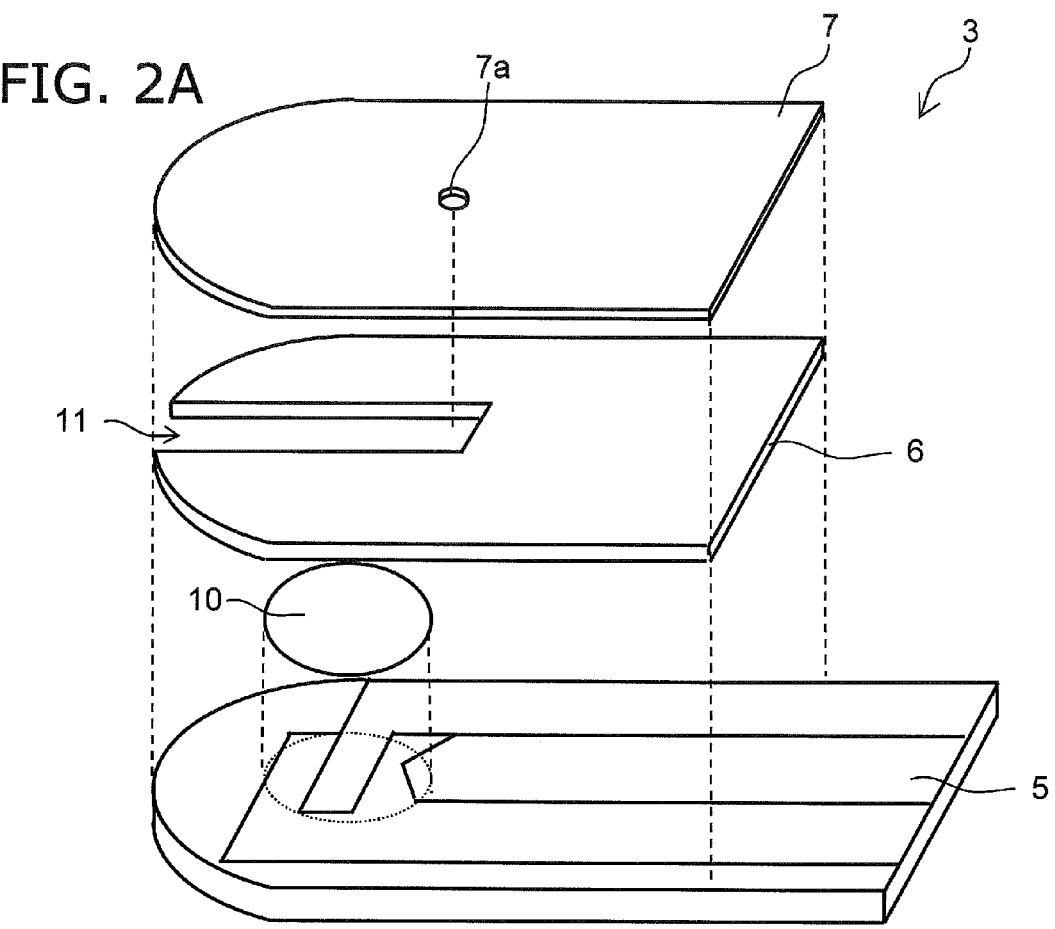
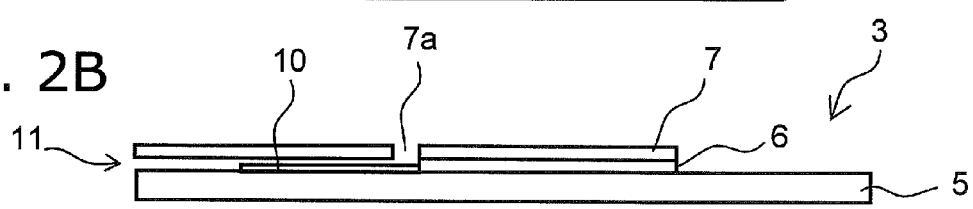
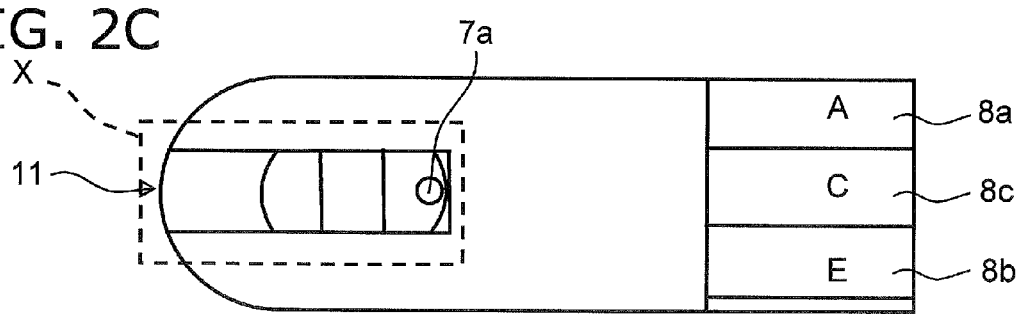

BIOLOGICAL SAMPLE MEASURING DEVICE

CROSS-REFERENCE TO RELATED APPLICATIONS

This application claims priority to PCT Application No. PCT/JP2012/001096, filed on Feb. 20, 2012, which in turn claims priority to Japanese Patent Application No. 2011-036647 filed on Feb. 23, 2011. The entire disclosures of PCT Application No. PCT/JP2012/001096 and Japanese Patent Application No. 2011-036647 are hereby incorporated by reference.

TECHNICAL FIELD

The present invention relates to a biological sample measuring device that measures information (blood glucose level, etc.) about a biological sample deposited on a sensor, for example.

BACKGROUND

Biological sample measuring devices that measure biological data, such as blood glucose level measurement devices for measuring blood glucose levels, have been used in the past.

These biological sample measuring devices are equipped with a biological sample measuring sensor that uses capillary action to introduce a biological sample deposited at the tip suction opening into a capillary. With a biological sample measuring device, biological sample information such as blood glucose level is measured by applying a specific voltage to the electrodes of the biological sample measuring sensor and measuring the output value from the output electrode.

For example, Japanese Laid-Open Patent Application 2003-4691 (laid open on Jan. 8, 2003) discloses an electrochemical sensor that tells the user to redo a test if there is not enough of a liquid sample containing the substance being analyzed.

SUMMARY

However, the following problems are encountered with the conventional sensor discussed above.

Specifically, with the sensor disclosed in the above-mentioned publication, a sub-element of a detecting electrode is provided farther up along the flow path of the biological sample than a working electrode, and when electrochemical continuity occurs between the working electrode and the sub-element and the current value exceeds an arbitrary threshold, it is determined that sufficient current is flowing to establish an effective test to measure the concentration of the biological sample, and measurement is commenced.

With this conventional sensor, however, the deposition observation time up to the point when the current value exceeds the arbitrary threshold is short (such as 1 to 5 seconds), and if the current value does not exceed the threshold during this brief deposition observation, it is concluded right away that an error has occurred. If this happens, that sensor has to be discarded, the patient's skin punctured again to collect a blood sample, and a new sensor used to measure again.

Meanwhile, there has been an increasing demand from users for a sensor that allows additional deposition to be performed even when the deposition observation time is extended and there is insufficient blood. However, if the deposition observation time is extended significantly beyond what it used to be (such as when it is extended from between 1 and 5 seconds to between 10 and 120 seconds), a biological sample that has seeped along the end inside the capillary (pass-around) will eventually reach the detecting electrode, causing the current value to exceed the threshold. When this happens, even though the capillary does not contain enough biological sample to perform accurate measurement, there is the risk that the system will mistakenly determine that a sufficient amount of biological sample is contained.

Also, when measurement is performed using blood as the biological sample, the plasma component of the blood may reach the electrode that detects the flow of blood while seeping into the reagent (seepage), even though there is an insufficient amount of blood for accurate measurement. Here again, the current value ends up exceeding a specific threshold, and there is the risk that the system will mistakenly determine that enough blood is contained.

It is an object of the present invention to provide a biological sample measuring device with which the degree to which a biological sample is introduced into the capillary of a sensor can be accurately detected, without being affected by pass-around or seepage.

The biological sample measuring device pertaining to a first embodiment includes a deposited biological sample introduced into a capillary, a biological sample measuring sensor, a mounting portion, a voltage application section, and a controller. The biological sample is deposited into the capillary by capillary action. In the biological sample measuring sensor, a reagent and the biological sample react. The reagent is mounted in the biological sample measuring sensor, and the biological sample is measured by the biological sample measuring sensor. The biological sample measuring device comprises a mounting portion, a voltage application section, and a controller. The biological sample measuring sensor is mounted to the mounting portion. The voltage application section applies voltage, used for measurement, to a plurality of electrodes disposed along the capillary in the biological sample measuring sensor. The controller eliminates the effect of seepage of the biological sample by seepage or pass-around at the end of the capillary, and detects the degree to which the biological sample is introduced into the capillary. The controller is able to eliminate these effects on the basis of the output result measured by applying voltage from the voltage application section to the electrodes.

When the first embodiment is in a state in which the biological sample is measured by applying voltage to the electrodes of the biological sample measuring sensor, the controller can determine how far into the capillary the biological sample has been introduced (the degree of introduction). This is detected by eliminating both the effect of infiltration of the biological sample by pass-around at the end of the capillary, and the effect of infiltration of the plasma component into the reagent by seepage based on of the output result for voltage applied to a plurality of electrodes provided along the capillary.

The term "pass-around" refers to a phenomenon whereby a biological sample infiltrates deep into the capillary along both ends in the width direction inside the tiny introduction space (capillary) provided for introducing the biological sample into the biological sample measuring sensor. The term "seepage" refers to a phenomenon whereby the plasma component of blood reaches a detecting electrode while seeping into the reagent when blood is being used as the biological sample.

For example, when pass-around occurs, if a biological sample of insufficient volume is deposited onto the sensor, such that the biological sample is not actually introduced onto the detecting electrode, there is the risk if misdetection if the capillary is filled by the biological sample as a result of the biological sample coming in at the ends of the capillary.

For example, when seepage occurs, if an insufficient volume of blood is deposited onto the sensor, such that the blood is not actually introduced onto the detecting electrode, there is the risk if misdetection if the capillary is filled by blood as a result of the plasma component in the blood seeping into the reagent while reaching the detecting electrode.

With the biological sample measuring device of the present invention, to eliminate misdetection and the introduction of biological sample due to this pass-around or seepage, the output result upon normal filling and the output result when pass-around or seepage occurs are determined on the basis of the output result when voltage was applied to a plurality of electrodes disposed along the capillary, which allows accurate detection of how far the biological sample has been introduced into the capillary.

The method for determining the output result upon normal filling, and the output result when pass-around or seepage occurs, can be as follows. Taking advantage of the fact that the characteristics of a function of elapsed time and output result vary greatly between normal filling and when pass-around or seepage occurs, whether the output result is for when the filling is normal or when pass-around or seepage occurs can be detected on the basis of the magnitude of the output value or the difference in the slope of the curves, for example.

Consequently, when only a small amount of biological sample has been deposited on the biological sample measuring sensor, and pass-around or seepage has occurred in a state in which the capillary is not sufficiently filled with biological sample, misdetection indicating that the proper amount of biological sample is contained, when pass-around or seepage has occurred, can be prevented by determining whether the output value was obtained as a result of pass-around, seepage, or was obtained as a result of normal filling. This allows for accurate detection of how far the biological sample has been introduced into the capillary.

As a result, even with a device having an auto-start function, a device can be prevented from automatically starting measurement by mistake when pass-around or seepage has occurred, which affords more accurate measurement.

The biological sample measuring device pertaining to a second embodiment includes the biological sample measuring device pertaining to the first embodiment, wherein further, the controller detects an additional deposit of the biological sample by detecting the peak of an output result that exceeds a specific threshold after it has been concluded that the capillary does not contain a sufficient quantity of the biological sample, the detection being a result of detecting the degree to which the biological sample was introduced.

Here, if it is learned that there is an insufficient volume of biological sample as a result of detecting the degree to which the biological sample was introduced, and after this the peak of the output value for voltage applied to the electrodes is detected, this is determined to be an additional deposit.

The term "additional deposit" here means that the user has noticed or been informed by the biological sample measuring device that the first deposited amount was insufficient, and the user adds more biological sample to the biological sample measuring sensor.

Consequently, even if measurement cannot be commenced, because it has been determined by detection of the above-mentioned degree of introduction of the biological sample that the capillary does not contain enough biological sample for measurement, and then the device subsequently detects an additional deposit, the device can automatically detect that the situation has changed to one that allows measurement.

For example, as a result, for a biological sample measuring device having an auto-start function, even if the volume of the biological sample deposited in the first deposit is insufficient, the system will prevent measurement from accidentally being started, due to the effect of pass-around, seepage, or the like, until the capillary is filled with biological sample and measurement becomes possible. Thus, measurement can automatically commence after waiting for an additional deposit.

The biological sample measuring device pertaining to a third embodiment includes the biological sample measuring device pertaining to the first or second embodiments, wherein the electrodes have a first electrode disposed farthest back inside the capillary, and a second electrode disposed in a region where the reagent is provided and more toward the inlet side of the capillary than the first electrode. The controller determines whether the capillary is in a properly filled state or in a state in which pass-around or seepage has occurred, on the basis of a function related to the slope of a graph showing the output result obtained by applying voltage between the first and second electrodes.

In the third embodiment, a function is used to determine whether the biological sample has been properly supplied, or pass-around or seepage has occurred. The function is related to the slope of a graph showing the output result. The output result is obtained by applying voltage between the first electrode and the second electrode. The first electrode is the farthest back in the capillary, and the second electrode is located at the reagent portion.

In the third embodiment, the proportional change in the output result, or the value of the output result after the elapse of a specific length of time expressed by the most characteristic difference between normal filling and when pass-around or seepage has occurred, can be detected to high precision by raising them to the n-th power, for example.

Consequently, the effect of pass-around or seepage will not cause misdetection of whether or not the biological sample has been introduced all the way from the portion where the reagent is located to the deepest part of the capillary, so accurate detection will be possible.

The biological sample measuring device pertaining to a fourth embodiment includes the biological sample measuring device pertaining to the first or second embodiments, wherein the electrodes include a first electrode disposed farthest back inside the capillary from the inlet, a second electrode disposed in a region where the reagent is provided, closer to the inlet side of the capillary than the first electrode, and a third electrode disposed closer to the inlet side of the capillary than the second electrode and between the first and second electrodes. The controller determines whether the capillary is in a properly filled state, or in a state in which pass-around or seepage has occurred, on the basis of a function related to the slope of a graph. The function related to the output result obtained by alternately applying voltage between the first and third electrodes, and between the second and the first electrodes, each for a specific length of time.

In the fourth embodiment, a function related to the slope of a graph showing the output result obtained by applying voltage alternately between the first electrode (the deepest part of the capillary) and the third electrode, and between the second electrode (at the reagent portion) and the first electrode, each for a specific length of time, is used to determine whether the output value obtained by applying voltage is the result of the biological sample being in a normal filling state or if it is the result of a state in which pass-around or seepage has occurred.

In the fourth embodiment, in which the function is related to the slope of the graph that serves as the basis for the above-mentioned determination, the proportional change in the output result, or the value of the output result after the elapse of a specific length of time expressed by the most characteristic difference between normal filling and when pass-around or seepage has occurred, can be detected to high precision by raising them to the n-th power, for example.

Consequently, accurate detection will be possible because pass-around or seepage will not cause misdetection of how far the biological sample has been introduced from the portion where the reagent is located to the deepest part of the capillary.

The biological sample measuring device pertaining a fifth embodiment includes the biological sample measuring device pertaining to the first or second embodiments, wherein the electrodes include a first electrode disposed farthest back inside the capillary, a second electrode disposed in a region where the reagent is provided, closer to the inlet side of the capillary than the first electrode, and a third electrode disposed closer to the inlet side of the capillary than the second electrode and between the first and second electrodes. The controller determines whether the capillary is in a properly filled state, or in a state in which pass-around or seepage has occurred, on the basis of a function related to the slope of a graph. The function being related to the output result obtained by applying voltage between the first and third electrodes.

In the fifth embodiment, a function related to the slope of a graph showing the output result obtained by applying voltage between the first electrode (the deepest part of the capillary) and the third electrode (disposed between the first and second electrodes and more toward the capillary inlet side than the second electrode) is used to determine whether the biological sample in the capillary is in a normally filled state or a state in which pass-around or seepage has occurred.

In the fifth embodiment, the function related to the slope of the graph that serves as the basis for the above-mentioned determination. The proportional change in the output result, or the value of the output result after the elapse of a specific length of time expressed by the most characteristic difference between normal filling and when pass-around or seepage has occurred, can be detected to high precision by raising them to the n-th power, for example.

Consequently, accurate detection will be possible because the effect of pass-around or seepage will not cause misdetection of whether the biological sample has been introduced all the way to the deepest part of the capillary.

The biological sample measuring device pertaining to a sixth embodiment includes the biological sample measuring device pertaining to any of the first to fifth embodiments, further comprising a display section that displays information related to the biological sample. The controller displays, on the display section, a display recommending an additional deposit of the biological sample. The controller determines whether to display the display on the basis of the detection result from detecting the degree to which the biological sample is introduced into the capillary.

In the sixth embodiment, after the degree of introduction of the biological sample into the capillary has been detected as discussed above, a display is shown to recommend to the patient or user an additional deposit of the biological sample.

Consequently, the patient, etc., can recognize right away that an insufficient volume of the biological sample was deposited at first, and can make an additional deposit, so that the biological sample measuring sensor is not wasted, and accurate measurement can be carried out.

The biological sample measuring device pertaining to a seventh embodiment includes the biological sample measuring device pertaining to any of the first to fifth embodiments, further comprising a display section that displays information related to the biological sample. The controller displays, on the display section, a measurement error display on the basis of the detection result for the degree to which the biological sample is introduced into the capillary.

In the seventh embodiment, after the degree of introduction of the biological sample into the capillary has been detected as discussed above, a measurement error display is given. The measurement error display indicates, to the patient or user, that an insufficient volume of the biological sample was deposited, and measurement is impossible.

Consequently, the patient, etc., can recognize right away that an insufficient volume of the biological sample was deposited at first, and can make an additional deposit. Thus, the biological sample measuring sensor is not wasted and accurate measurement can be carried out.

With the biological sample measuring device pertaining to the present invention, even if an insufficient volume of the biological sample was deposited on the biological sample measuring sensor, and the capillary is not sufficiently filled with the biological sample, misdetection of the biological sample due to pass-around or seepage can be prevented by providing accurate detection of how far into the capillary the biological sample has been introduced.

BRIEF DESCRIPTION OF DRAWINGS

FIG. 2A is an exploded oblique view of the biological sample measuring sensor used in the biological sample measuring device in FIG. 1, FIG. 2B is a side cross section thereof, and FIG. 2C is a plan view thereof;

DETAILED DESCRIPTION

Selected embodiments will now be explained with reference to the drawings. It will be apparent to those skilled in the art from this disclosure that the following descriptions of the embodiments are provided for illustration only and not for the purpose of limiting the invention as defined by the appended claims and their equivalents.

Embodiment 1

The biological sample measuring device pertaining to an embodiment of the present invention will be described through reference to FIGS. 1 to 6F.

Configuration of Biological Sample Measuring Device

Figure 1:
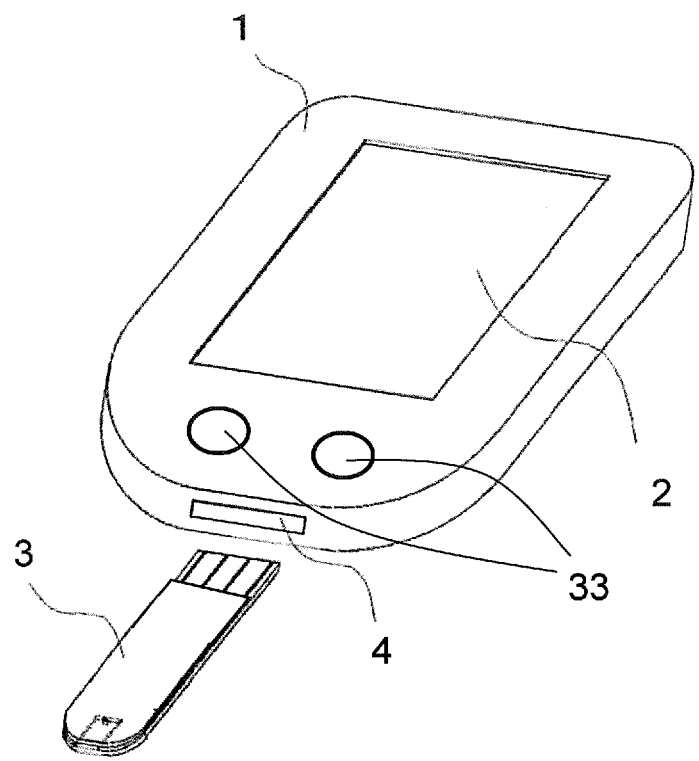
FIG. 1 is an oblique view of the biological sample measuring device pertaining to an embodiment of the present invention.

As shown in FIG. 1, the biological sample measuring device pertaining to this embodiment comprises a main body case 1, a display section 2 and control buttons 33 provided on the front of the main body case 1, and a mounting portion 4 for a biological sample measuring sensor 3 provided at the lower end of the main body case 1.

Configuration of Biological Sample Measuring Sensor 3

As shown in FIGS. 2A to 2C, the biological sample measuring sensor 3 consists of a substrate 5, a spacer 6, and a cover 7 that are stacked and integrated. FIG. 2A is a developed oblique view of the biological sample measuring sensor 3, FIG. 2B is a cross section of the biological sample measuring sensor 3 as seen from the side face, and FIG. 2C is a plan view of the biological sample measuring sensor 3 (in a state in which there is no cover 7).

The substrate 5 is a flat member that serves as the base of the biological sample measuring sensor 3, and on its top face are provided an electrode 8A (second electrode), an electrode 8B (third electrode), and an electrode 8C (first electrode).

A reagent 10 that reacts with blood or another such biological sample is provided on the side of the electrodes 8A to 8C on which the biological sample is deposited.

The spacer 6 is disposed so as to be sandwiched between the substrate 5 and the cover 7, and has a groove 11 at the end on the side where the biological sample is deposited. The substrate 5, the spacer 6, and the cover 7 are integrated so that the groove 11 portion functions as a capillary, which is a path for introducing the biological sample.

Capillary action causes the blood or other biological sample that is deposited on the biological sample measuring sensor 3 to advance deeper into the groove 11 functioning as a capillary. Once the biological sample reaches the reagent 10 portion, a reaction occurs between the reagent 10 and a specific component included in the biological sample (such as the glucose in blood). With the biological sample measuring device in this embodiment, information related to the biological sample, such as the blood glucose level, is measured on the basis of this reaction value.

As shown in FIGS. 2A to 2C, the substrate 5 is longer than the spacer 6 and the cover 7 in the lengthwise direction. Consequently, the ends of the electrodes 8A to 8C provided to the substrate 5 that are on the opposite side from the side where the biological sample is deposited are exposed outside the sensor. Accordingly, the biological sample measuring sensor 3 can be electrically connected with the electrical circuit inside the main body case 1 merely by mounting the mounting portion 4 to the mounting portion 4 of the main body case 1.

The cover 7 has an air hole 7a that promotes capillary action within the capillary, at a location corresponding to the inner end of the groove 11 of the spacer 6.

As shown in FIG. 2B, the air hole 7a is disposed further to the inside (the right side in FIG. 2) than the location where the reagent 10 is placed on the biological sample measuring sensor 3. Consequently, the blood or other biological sample deposited on the distal end side (the left side in FIG. 2) of the capillary can be introduced smoothly up to the location of the reagent 10 by capillary action.

Figure 3:
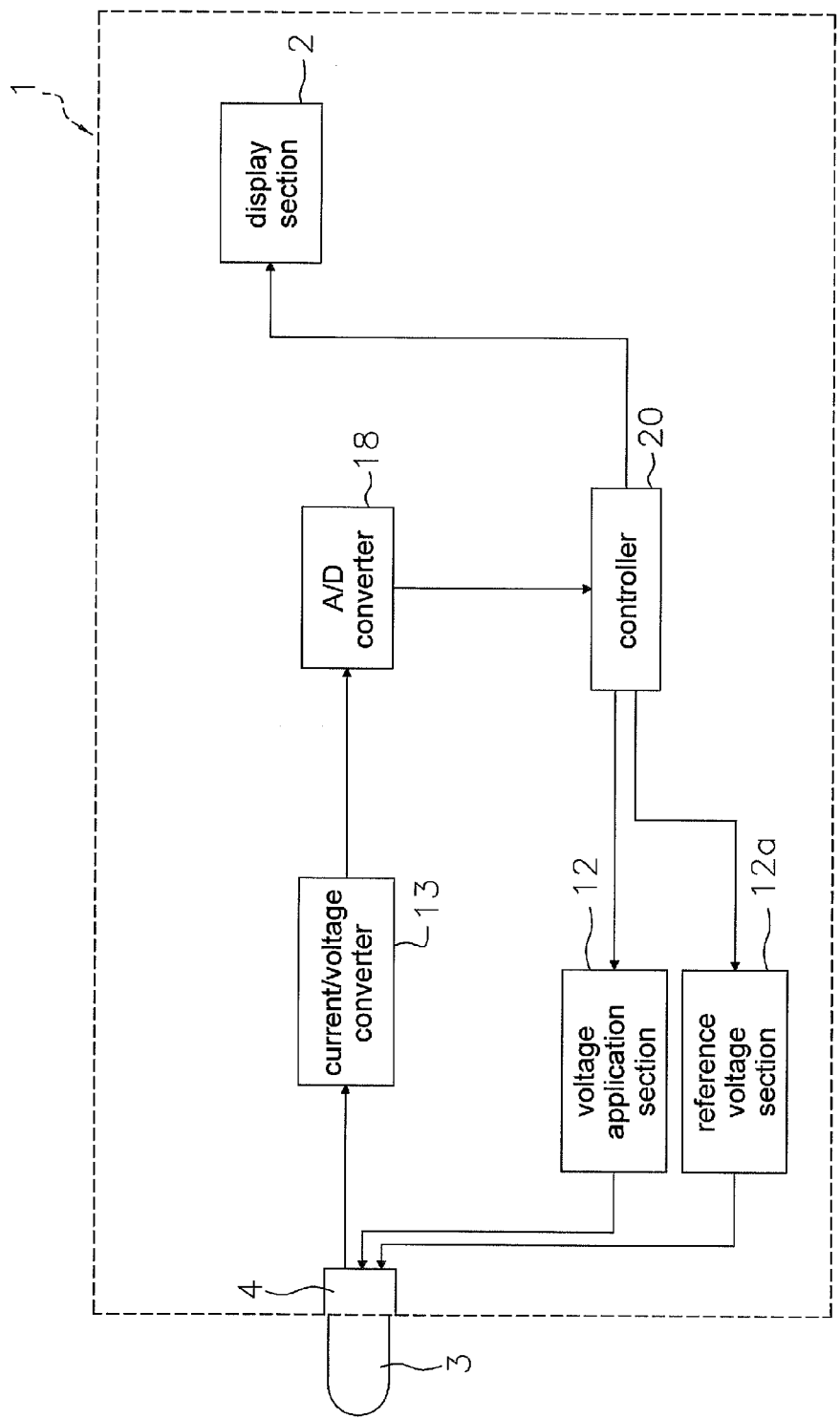
FIG. 3 is a control block diagram of the biological sample measuring device in FIG. 1.

In a state in which the biological sample measuring sensor 3 has been mounted, the electrodes 8A to 8C are connected to a voltage application section 12 and a current/voltage converter 13 provided on the biological sample measuring device side (see FIG. 3).

Configuration of Biological Sample Measuring Device

As shown in the control block diagram of FIG. 3, the biological sample measuring device in this embodiment comprises, inside the main body case 1, the mounting portion 4 to which the above-mentioned biological sample measuring sensor 3 is mounted, the voltage application section 12, a reference voltage section 12A, the current/voltage converter 13, an A/D (analog/digital) converter 18, a controller 20, a memory 23, and the display section 2.

The display section 2 displays biological sample measurement values (such as the blood glucose level), messages recommending an additional deposit (discussed below), measurement error, and various other such information.

The voltage application section 12 is connected to the mounting portion 4 to which the biological sample measuring sensor 3 is mounted, and applies a specific voltage to the electrodes of the biological sample measuring sensor 3.

The reference voltage section 12A applies a reference voltage to the terminal serving as the counter electrode of the biological sample measuring sensor 3. Consequently, there is a different between the voltages applied to the two ends of the biological sample measuring sensor 3, namely, the voltage applied from the voltage application section 12 and the voltage applied from the reference voltage section 12A.

The current/voltage converter 13 is connected to the mounting portion 4 to which the biological sample measuring sensor 3 is mounted, and converts the current value outputted from the output electrode of the biological sample measuring sensor 3 into a voltage value as a result of a specific voltage being applied from the voltage application section 12 and the reference voltage section 12A.

The A/D converter 18 is connected to the output side of the voltage application section 13, receives signals outputted from the voltage application section 13, and is connected to the controller 20.

The controller 20 controls the display section 2, the voltage application section 12, and the reference voltage section 12A by referring to threshold data and the like stored in the memory 23 and to the output value from the A/D converter 18. The auto-start control based on the threshold determination prior to the start of measurement by the controller 20 will be discussed in detail at a later stage.

The memory 23 holds threshold data, measurement values, computational formulas, and the like that are necessary when performing the threshold determination discussed below, and is used by the controller 20 to take out required data as needed.

Auto-Start Control

Figure 4:
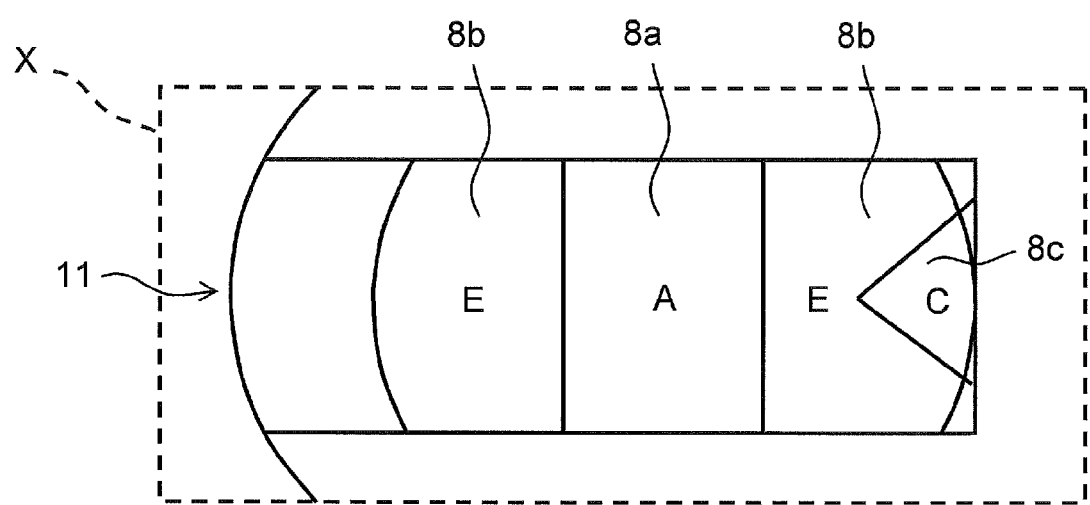
FIG. 4 is a detail view of the X portion in FIG. 2C.

As shown in FIG. 4, with the biological sample measuring device in this embodiment, a specific voltage is applied to the electrodes 8A to 8C disposed so as to be exposed within the capillary of the biological sample measuring sensor 3. On the basis of this output result, it is determined whether or not the capillary is sufficiently filled with the biological sample deposited on the biological sample measuring sensor 3, and auto-start control is performed so that measurement does not start until a sufficiently filled state is attained.

As shown in FIG. 4, a plurality of electrodes 8A to 8C are provided to the biological sample measuring sensor 3 along the lengthwise direction of the capillary (the groove 11). Here, the electrode disposed at the portion where the reagent 10 is disposed is called the A electrode, the electrode 8C disposed at the deepest part of the capillary is called the C electrode, and the electrodes 8B disposed so as to sandwich the electrode 8A (the A electrode) is called the E electrode.

With the biological sample measuring device in this embodiment, a specific voltage is applied between the A and C electrodes (the electrodes 8A and 8C) prior to starting the measurement of the biological sample (such as measurement of glucose concentration), and if it is detected that not enough of the biological sample fills the capillary of the biological sample measuring sensor 3, auto-start control is performed so that measurement is not automatically started until the biological sample reaches a sufficiently filled state.

With conventional auto-start control, first voltage is applied between the A and E electrodes, the biological sample is introduced up to between the A and E electrodes and reacts with the reagent, and the system waits until the output value exceeds a threshold (preferably a voltage of 10 to 50 mV, such as 15 mV). Once the output value exceeds the above-mentioned threshold, the electrodes to which the voltage is applied are switched to between the A and C electrodes, and if the output value exceeds a threshold (preferably a voltage of 10 to 50 mV, such as 20 mV), the measurement of glucose or the like is commenced. The set value for the threshold used in executing this auto-start function preferably varies with the ambient temperature during measurement. For example, if the ambient temperature is below Temp1 (such as 15° C.), the reaction between the biological sample and the reagent will be slow, so the threshold of the output value of the voltage applied between the A and E electrodes (preferably a voltage of 5 to 30 mV, such as 7 mV), and the threshold of the output value of the voltage applied between the A and C electrodes (preferably a voltage of 5 to 30 mV, such as 10 mV) are used.

Figure 5:
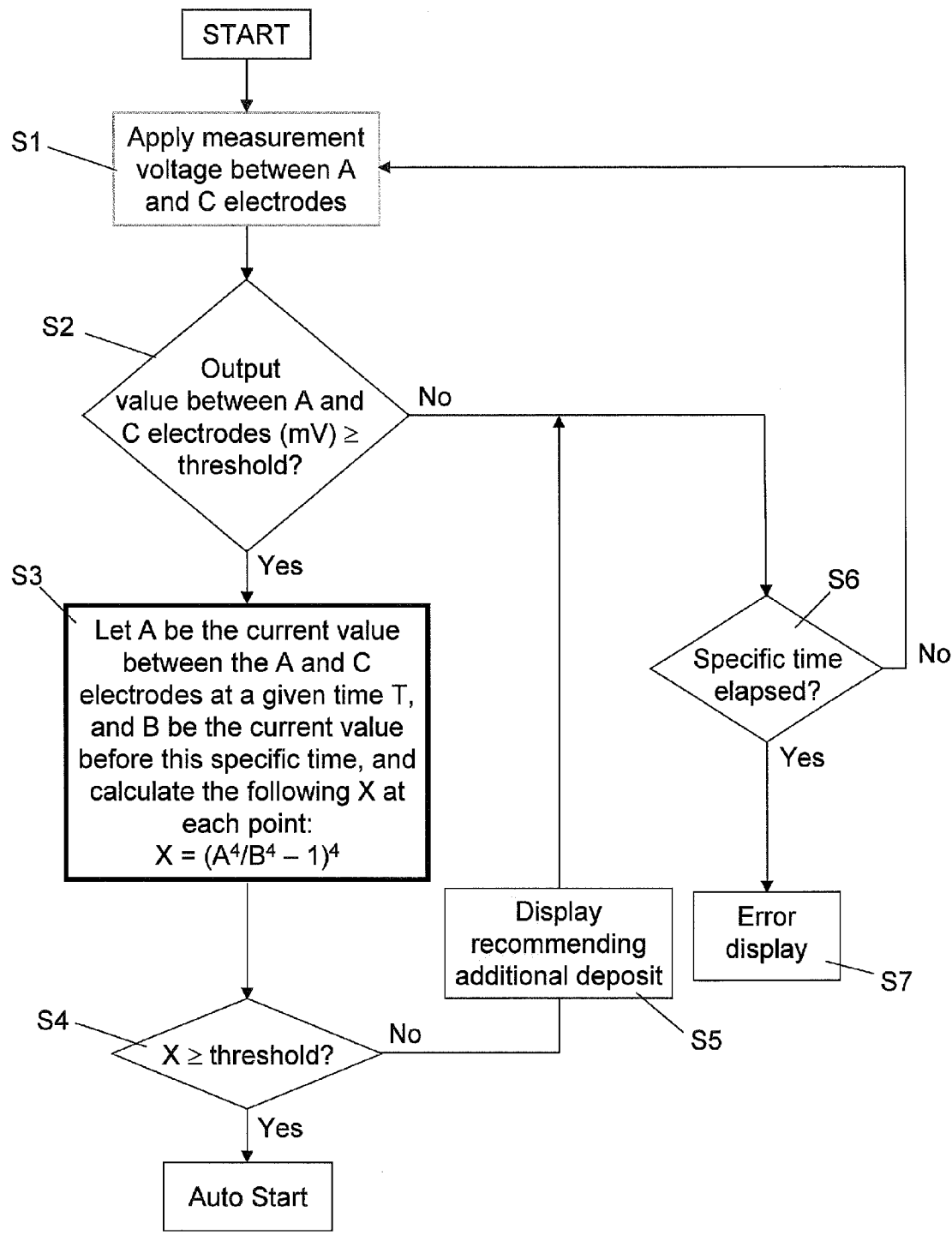
FIG. 5 is a flowchart of the flow in auto-start control by the biological sample measuring device in FIG. 1.

In this embodiment, auto-start control is executed according to the flowchart in FIG. 5.

More specifically, first, in step S1, a specific voltage V1 (preferably a voltage of 150 mV to 1.0 V, such as 500 mV) is applied between the A and C electrodes. This specific voltage V1 is what is applied to detected whether or not the capillary has been filled with the biological sample.

Next, in step S2, the system waits until the output value produced by applying voltage between the A and C electrodes (expressed as the voltage value after converting the output current into voltage) reaches or exceeds a specific threshold V2 (preferably a voltage of 1 to 30 mV, such as 12 mV).

We will assume that the output value being described here is (voltage value after current-voltage conversion: mV)=current value (μA)×30 (kΩ: resistance).

Once a specific length of time (preferably between 10 and 120 seconds, such as 30 seconds) has elapsed without any change, the flow proceeds to step S6, and in step S7 the controller 20 controls the display section 2 so that it displays a measurement error.

Next, when the output current exceeds the above-mentioned threshold V2, in step S3 a value X used in threshold determination is calculated. More specifically, if we let A be the output value at a given time T, and B be the output value before this specific time (preferably within 0.01 to 2 seconds, such as 0.1 second), a computation value X is calculated at each point.

The computation value X here is calculated from the following relational formula.

$$X = (A^4/B^4 - 1)^4 \quad (1)$$

Specifically, the value X here is calculated by subtracting "1" from the ratio of values of raising the output current values A and B to the fourth power, and then further raising this remainder to the fourth power.

In the above relational formula (1), the reason for raising the output current values A and B, etc., to the fourth power is to improve the accuracy of threshold determination used to more accurately detect whether or not the capillary has been sufficiently filled with the biological sample.

Figure 6A:
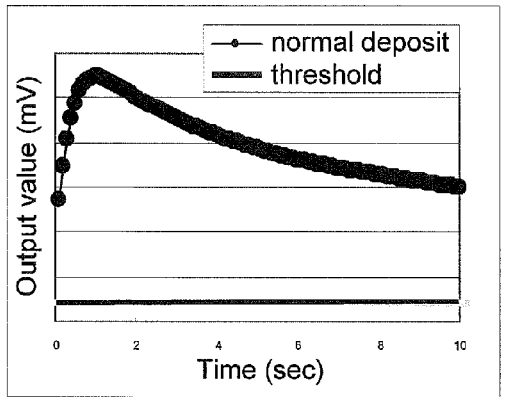
FIG. 6A is a graph of the output result versus elapsed time when just a normal amount of biological sample has been deposited on a sensor in the biological sample measuring device in FIG. 1.
Figure 6D:
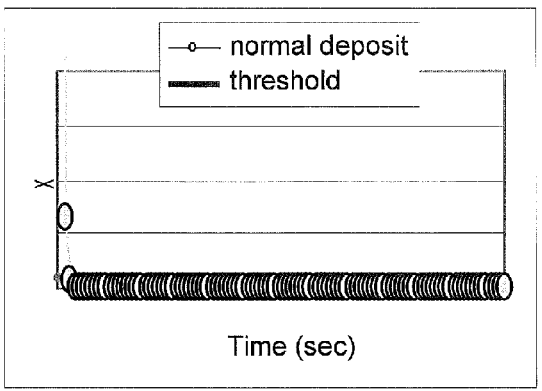
FIGS. 6D to 6F are graphs of the relation between the value of X and the elapsed time corresponding to FIGS. 6A to 6C.
Figure 6B:
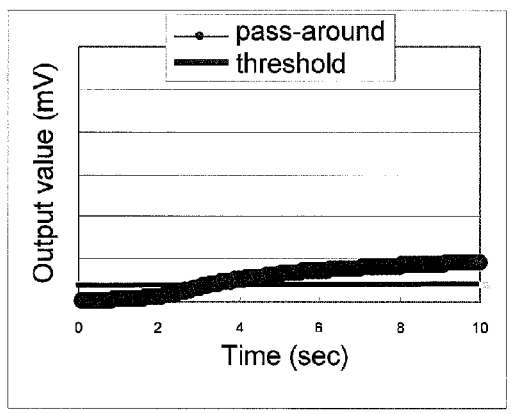
FIG. 6B is a graph of the output result versus elapsed time when there is not enough biological sample and pass-around or seepage has occurred.

The graphs in FIGS. 6A and 6B are the basis for being able to detect the degree of introduction of the biological sample in the capillary by threshold determination using the value X calculated in the above relational formula (1).

FIG. 6A is a graph of the relation between the output current value and elapsed time with a normal deposit, in which a sufficient amount of biological sample has been deposited on the sensor and the capillary has been sufficiently filled.

The "sufficient amount" referred to above is an amount at which the reaction needed for measurement occurs adequately, and means an amount of biological sample sufficient to cover the entire working electrode inside the capillary. This will vary with the volume of the capillary and the layout of the working electrode or other detecting electrodes in the capillary, but is preferably at least 50% of the volume of the capillary. More preferable is 80% or more. For example, if the volume of the capillary is 0.6 µL, then 0.5 µL or more will be a sufficient amount.

FIG. 6B is a graph of the relation between the output current value and elapsed time in a state in which an insufficient amount of biological sample (such as less than 0.5 µL) has been deposited on the sensor and the capillary has not been sufficiently filled, so that pass-around or seepage occurs.

Specifically, when a sufficient amount of biological sample has been deposited on the biological sample measuring sensor 3, as shown in FIG. 6A, a reaction occurs right away between the reagent 10 and the biological sample filling the capillary, and the result is a graph in which the output current value also rises at the initial stage. On the other hand, if a sufficient amount of biological sample has not been deposited on the biological sample measuring sensor 3, as shown in FIG. 6B, a reaction does not occur right away between the reagent 10 and the biological sample filling the capillary, and instead a reaction occurs gradually between the reagent 10 and the biological sample that has gradually infiltrated deep into the capillary due pass-around or seepage, the result of which is a graph in which the output current value remains at a low level while rising a little at a time.

In this embodiment, we focus on the fact that there is a major difference in the proportional change in output current value versus elapsed time (the slope of the graph) between when a sufficient amount of biological sample was deposited (see FIG. 6A) and when an insufficient amount of biological sample was deposited and pass-around or seepage occurred (see FIG. 6B), and use a numerical value X that clearly represents this difference to compare with a specific threshold.

That is, in step S4, the value X calculated in step S3 is compared to a preset threshold. Here, when the value X is greater than or equal to the threshold, it is concluded that the capillary is filled with a sufficient amount of biological sample, and measurement voltage is applied to the electrodes 8A to 8C to start measurement automatically.

More specifically, when a sufficient amount of biological sample has been deposited (with a normal deposit), as shown in FIG. 6D, the value X exceeds the threshold immediately after the application of voltage. Consequently, the controller 20 controls the voltage application section 12 so that voltage for starting measurement automatically will be applied.

On the other hand, in step S4, if the value X is below the threshold, it is concluded that the capillary is not filled with a sufficient amount of biological sample, and that the detected current value is one that accompanies pass-around or seepage, so the flow moves to step S5.

Figure 6E:
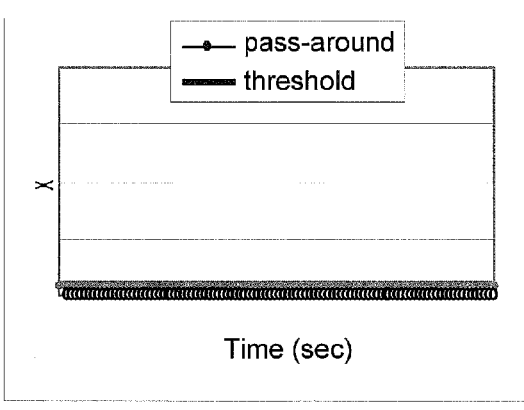

More specifically, when an insufficient amount of biological sample has been deposited and pass-around or seepage has occurred, as shown in FIG. 6E, the value X does not exceed the threshold. Consequently, the controller 20 controls the voltage application section 12 so as not to apply voltage for mistakenly starting measurement automatically.

Next, in step S5, the controller 20 receives the result of threshold determination in step S3 and controls the display section 2 so as to give a display recommending that the patient make an additional deposit.

The threshold used in threshold determination is preferably set according to the ambient temperature during measurement. As a specific example of this, when the ambient temperature T is below 20° C., the threshold is set to 0.2, when the ambient temperature T is at least 20° C. but below 30° C., the threshold is set to 0.5, and when the ambient temperature T is at least 30° C., the threshold is set to 1.2. The threshold is changed depending on the ambient temperature, and the degree of introduction of the biological sample is determined by comparison to the above-mentioned value X.

Consequently, even if the output current value changes due to a difference in the extent to which the reaction between the biological sample and the reagent 10 proceeds depending on how high or low the ambient temperature is, auto-start control can still be carried out very accurately regardless of changes in the ambient temperature.

A case was described here in which the temperature range (5 to 45 degrees) over which measurement is possible with the biological sample measuring device of this embodiment was divided in three, but the present invention is not limited to this. For example, the range may be divided in two or less, or may be divided more finely into four or more parts.

Figure 6C:
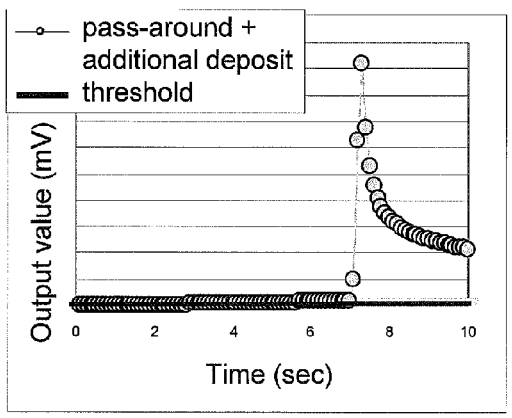
FIG. 6C is a graph of the output result versus elapsed time when an additional deposit has been made.

In step S5, if the patient makes an additional deposit of biological sample because of a display recommending additional deposit, the capillary will be filled all at once with biological sample that will then react with the reagent 10, so as shown in FIG. 6C, the output current value rises sharply and appears as the peak current.

Figure 6F:
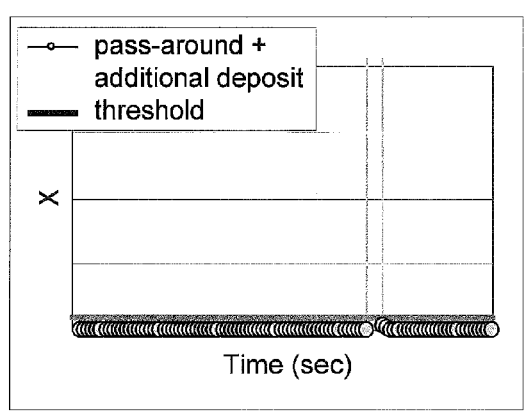

As shown in FIG. 6F, in this embodiment the filling state inside the capillary after additional deposit can be detected by detecting the peak current at which the value X calculated from the above-mentioned relational formula (1) exceeds the threshold. The threshold set for use in detecting the peak current may also be used in the detection of this peak current.

The thresholds in the graphs in FIGS. 6A and 6B are the ones used in conventional auto-start control.

That is, when auto-start control is carried out with this conventional threshold setting alone, then even though the capillary has not been sufficiently filled with biological sample, if the output current value obtained as a result of biological sample infiltrating to the ends of the capillary by pass-around or seepage and gradually reacting with the reagent 10 should end up being detected and exceeding the threshold (after 3 seconds have elapsed in FIG. 6B), measurement will end up being commenced automatically. If measurement is performed by applying measurement voltage to this insufficient amount of biological sample, there is the risk that the obtained measured value will be lower than the actual value.

With the biological sample measuring device in this embodiment, to accurately detect the degree to which a biological sample is introduced into the capillary, a value X is calculated from a function (Relational Formula 1) using numerical values A and B related to the slope of the graphs shown in FIGS. 6A and 6B, and threshold determination is carried out by comparing the value X with the threshold as shown in FIGS. 6D and 6E.

Consequently, whether or not the capillary has been sufficiently filled with biological sample (the degree of introduction of biological sample) can be detected more accurately by eliminating the effect of pass-around or seepage, as compared to conventional threshold determination in which the measurement result simply compared to a threshold. As a result, this avoids the automatic starting of measurement until there is an additional deposit and the capillary is filled with a sufficient amount of biological sample, so very accurate auto-start control can be performed.

Also, with the biological sample measuring device in this embodiment, as shown in FIGS. 6C and 6F, there is a function for detecting that there was an additional deposit or a display recommending an additional deposit (step S5).

Consequently, rather than merely detecting whether or not the capillary contains enough biological sample for measurement, the user can be urged to make an additional deposit so as to create a state in which measurement is possible, just by using the same sensor. As a result, there is no need to discard the biological sample measuring sensor 3 just because there was not enough biological sample at the time of the first deposit, so the biological sample measuring sensor 3 can be used more efficiently, without being wasted.

Embodiment 2

The biological sample measuring device pertaining to another embodiment of the present invention will be described through reference to FIGS. 7 and 8A to 8F.

In this embodiment, using a device with the same configuration as that of the biological sample measuring device used in Embodiment 1 above, another relational formula is used to calculate a value X on the basis of the result of applying voltage between different electrodes (between the C and E electrodes, and between the A and C electrodes) from those in Embodiment 1 (between the A and C electrodes), and auto-start control is carried out. Thus, in this embodiment, the basic flow is the same as that in the flowchart shown in FIG. 5 and described in Embodiment 1 above, so only the portions that are different will be described below, and description of shared portions will be omitted.

Specifically, in this embodiment, of the electrodes 8A, 8B, and 8C shown in FIG. 4, auto-start control is carried out by applying voltage alternately and at specific time intervals between the electrode 8C (first electrode) disposed at the deepest part of the capillary and the electrodes 8B (third electrodes) that are disposed between the electrodes 8A and 8C and more toward the capillary inlet side than the electrode 8A, as well as between the electrode 8A (second electrode) disposed in the region where the reagent 10 is provided and more toward the capillary inlet side than the electrode 8C, and the above-mentioned electrode 8C (first electrode).

Figure 7:
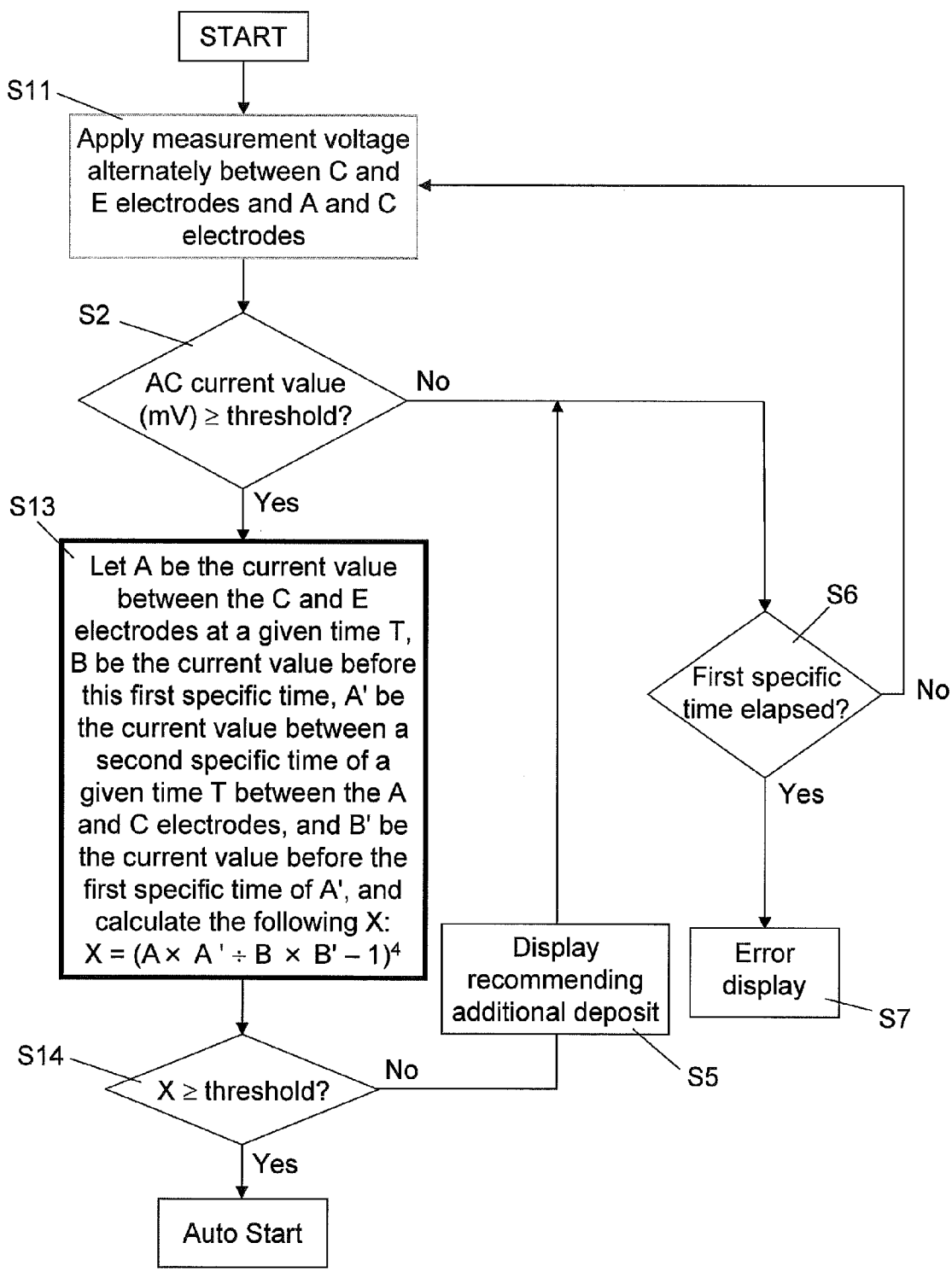
FIG. 7 is a flowchart of the flow in auto-start control by the biological sample measuring device pertaining to another embodiment of the present invention.

More specifically, as shown in step S11 in FIG. 7, the controller 20 determines whether the capillary is in a properly filled state or a state in which pass-around or seepage has occurred, on the basis of graphs (see FIGS. 8A and 8B) of the output result obtained by alternately applying a specific voltage (preferably within a range of 150 mV to 1V, such as 500 mV) at specific time intervals (preferably within a range of 0.01 to 2 seconds, such as every 0.1 second) between the electrodes 8C and 8B (the C and E electrodes) and between the electrodes 8A and 8C (the A and C electrodes).

That is, in this embodiment, just as in Embodiment 1 above, we focus on the fact that there is a major difference in the proportional change in output current value versus elapsed time (the slope of the graph) between when a sufficient amount of biological sample was deposited (see FIG. 8A) and when an insufficient amount of biological sample was deposited and pass-around or seepage occurred (see FIG. 8B), and use a numerical value X that clearly represents this difference to compare with a specific threshold.

More specifically, as shown in step S13 in FIG. 7, if we let A be the output current value with respect to the voltage applied between the C and E electrodes at a given time T, and B be the output current value with respect to the voltage applied between the C and E electrodes before this first specific time (preferably within 0.01 to 2 seconds, such as 0.2 second), and if we let A' be the output current value with respect to the voltage applied between the A and C electrodes before a second specific time of the above-mentioned time T (preferably within 0.01 to 2 seconds, such as 0.1 second), and B' be the output current value with respect to the voltage applied between the A and C electrodes before this first specific time (preferably within 0.01 to 2 seconds, such as 0.2 second), a value X is calculated on the basis of the following relational formula (2).

$$X=(A \times A'/B \times B'-1)^4 \qquad (2)$$

Specifically, the value X here is calculated by subtracting "1" from the product of multiplying the output current values A and A', and B and B', and raising this remainder to the fourth power.

In the above-mentioned relational formula (2), the reason for raising to the fourth power the numerical value obtained by subtracting 1 from the ratio of $(A \times A')$ and $(B \times B')$ is the same as with Relational Formula 1 in Embodiment 1 above, to improve the accuracy of threshold determination for accurately detecting whether or not the capillary has been sufficiently filled with biological sample.

In this embodiment, as shown in the flowchart in FIG. 7, first in step S11 a specific voltage (preferably within a range of 150 mV to 1 V, such as 500 mV) is applied alternately between the C and E electrodes and between the A and C electrodes.

Step S2 is the same as in the flowchart in FIG. 5 in Embodiment 1 above.

Then, in step S13, the value X is calculated on the basis of the above-mentioned relational formula (2).

Next, in step S14, the value X calculated in step S13 is compared to a preset threshold. Here, when the value X is greater than or equal to the threshold, it is concluded that the capillary is filled with a sufficient amount of biological sample, and measurement voltage is applied to the electrodes 8A to 8C to start measurement automatically.

Figure 8A:
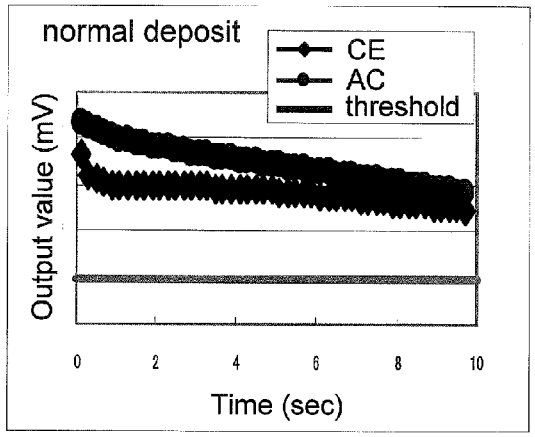
FIG. 8A is a graph of the output result versus elapsed time when just a normal amount of biological sample has been deposited on a sensor in the biological sample measuring device in another embodiment of the present invention.
Figure 8D:
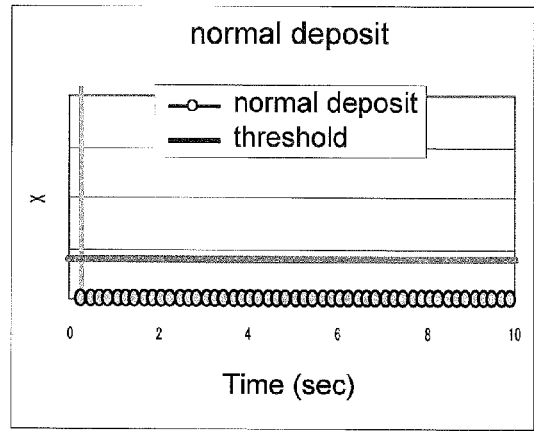
FIGS. 8D to 8F are graphs of the relation between the value of X and the elapsed time corresponding to FIGS. 8A to 8C.

More specifically, when a sufficient amount of biological sample has been deposited (with a normal deposit), as shown in FIG. 8D, the value X exceeds the threshold immediately after the application of voltage. Consequently, the controller 20 controls the voltage application section 12 so that voltage for starting measurement automatically will be applied. On the other hand, if an insufficient amount of biological sample has been deposited and pass-around or seepage has occurred, the value X will not exceed the threshold, as shown in FIG.

8E. Consequently, the controller 20 controls the voltage application section 12 so that no voltage is applied by mistake for starting measurement automatically.

The flow from step S5 and beyond is the same as in Embodiment 1 above, and therefore will not be described again here.

The threshold used during threshold determination in step S14 is preferably set according to the ambient temperature during measurement. As a specific example of this, when the ambient temperature T is below 20° C., the threshold is set to 2, when the ambient temperature T is at least 20° C. but below 30° C., the threshold is set to 4, and when the ambient temperature T is at least 30° C., the threshold is set to 8. The threshold is changed depending on the ambient temperature, and the degree of introduction of the biological sample is determined by comparison to the above-mentioned value X.

Consequently, even if the output current value changes due to a difference in the extent to which the reaction between the biological sample and the reagent 10 proceeds depending on how high or low the ambient temperature is, auto-start control can still be carried out very accurately regardless of changes in the ambient temperature.

A case was described here in which the temperature range (5 to 45 degrees) over which measurement is possible with the biological sample measuring device of this embodiment was divided in three, but the present invention is not limited to this. For example, the range may be divided in two or less, or may be divided more finely into four or more parts.

Figure 8B:
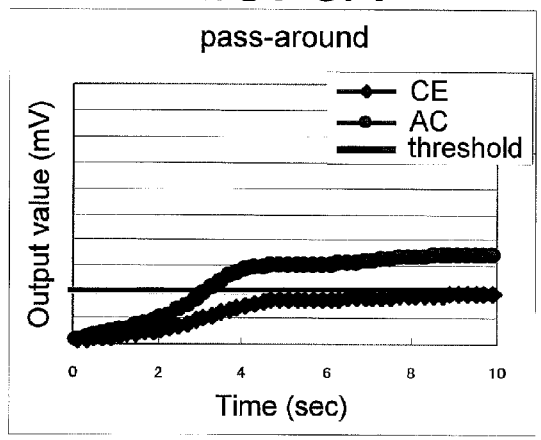
FIG. 8B is a graph of the output result versus elapsed time when there is not enough biological sample and pass-around or seepage has occurred.
Figure 8E:
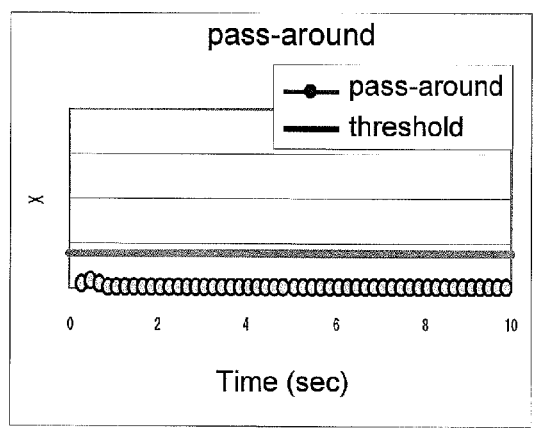
Figure 8C:
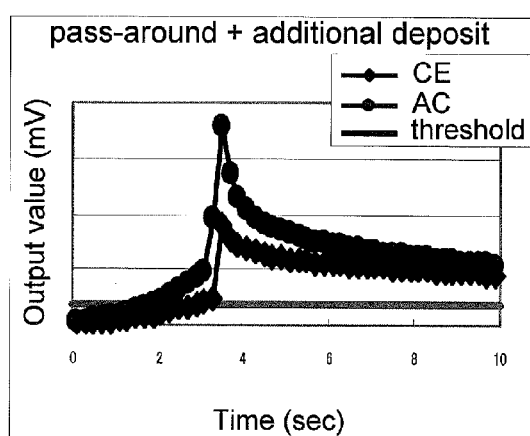
FIG. 8C is a graph of the output result versus elapsed time when an additional deposit has been made.

In step S5, if the patient makes an additional deposit of biological sample on the biological sample measuring sensor 3 because of a display recommending additional deposit, the capillary will be filled all at once with biological sample that will then react with the reagent 10, so as shown in FIG. 8C, the output current value rises sharply and appears as the peak current.

Figure 8F:
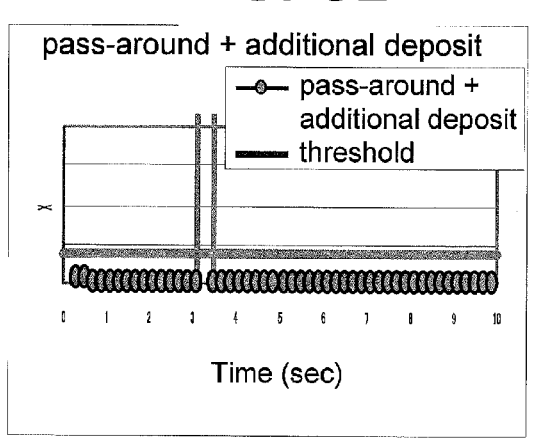

As shown in FIG. 8F, in this embodiment the filling state inside the capillary after additional deposit can be detected by detecting the peak current at which the value X calculated from the above-mentioned relational formula (2) exceeds the threshold. The threshold set for use in detecting the peak current may also be used in the detection of this peak current.

The thresholds in the graphs in FIGS. 8A and 8B are the ones used in conventional auto-start control.

That is, when auto-start control is carried out with this conventional threshold setting alone, then even though the capillary has not been sufficiently filled with biological sample, if the output current value obtained as a result of biological sample infiltrating to the ends of the capillary by pass-around or seepage and gradually reacting with the reagent 10 should end up being detected and exceeding the threshold, measurement will end up being commenced automatically (see FIG. 8B). If measurement is performed by applying measurement voltage to this insufficient amount of biological sample, there is the risk that the obtained measured value will be lower than the actual value.

With the biological sample measuring device in this embodiment, to accurately detect the degree to which a biological sample is introduced into the capillary, a value X is calculated from a function (Relational Formula 2) related to the slope of the graphs shown in FIGS. 8A and 8B, and threshold determination is carried out by comparing the value X with the threshold as shown in FIGS. 8D and 8E.

Consequently, whether or not the capillary has been sufficiently filled with biological sample (the degree of introduction of biological sample) can be detected more accurately by eliminating the effect of pass-around or seepage, as compared to conventional threshold determination in which the measurement result simply compared to a threshold. As a result, this avoids the automatic starting of measurement until there is an additional deposit and the capillary is filled with a sufficient amount of biological sample, so very accurate auto-start control can be performed.

Embodiment 3

The biological sample measuring device pertaining to yet another embodiment of the present invention will be described through reference to FIGS. 9 and 10A to 10F.

In this embodiment, using a device with the same configuration as that of the biological sample measuring device used in Embodiment 1 above, another relational formula is used to calculate a value X on the basis of the result of applying voltage between different electrodes (between the C and E electrodes) from those in Embodiment 1 (between the A and C electrodes), and auto-start control is carried out. Thus, in this embodiment, the basic flow is the same as that in the flowchart shown in FIG. 5 and described in Embodiment 1 above, so only the portions that are different will be described below, and description of shared portions will be omitted.

Specifically, in this embodiment, of the electrodes 8A, 8B, and 8C shown in FIG. 4, auto-start control is carried out by applying voltage between the electrode 8C (first electrode) disposed at the deepest part of the capillary and the electrodes 8B (third electrodes) that are disposed between the electrodes 8A and 8C and more toward the capillary inlet side than the electrode 8A.

Figure 9:
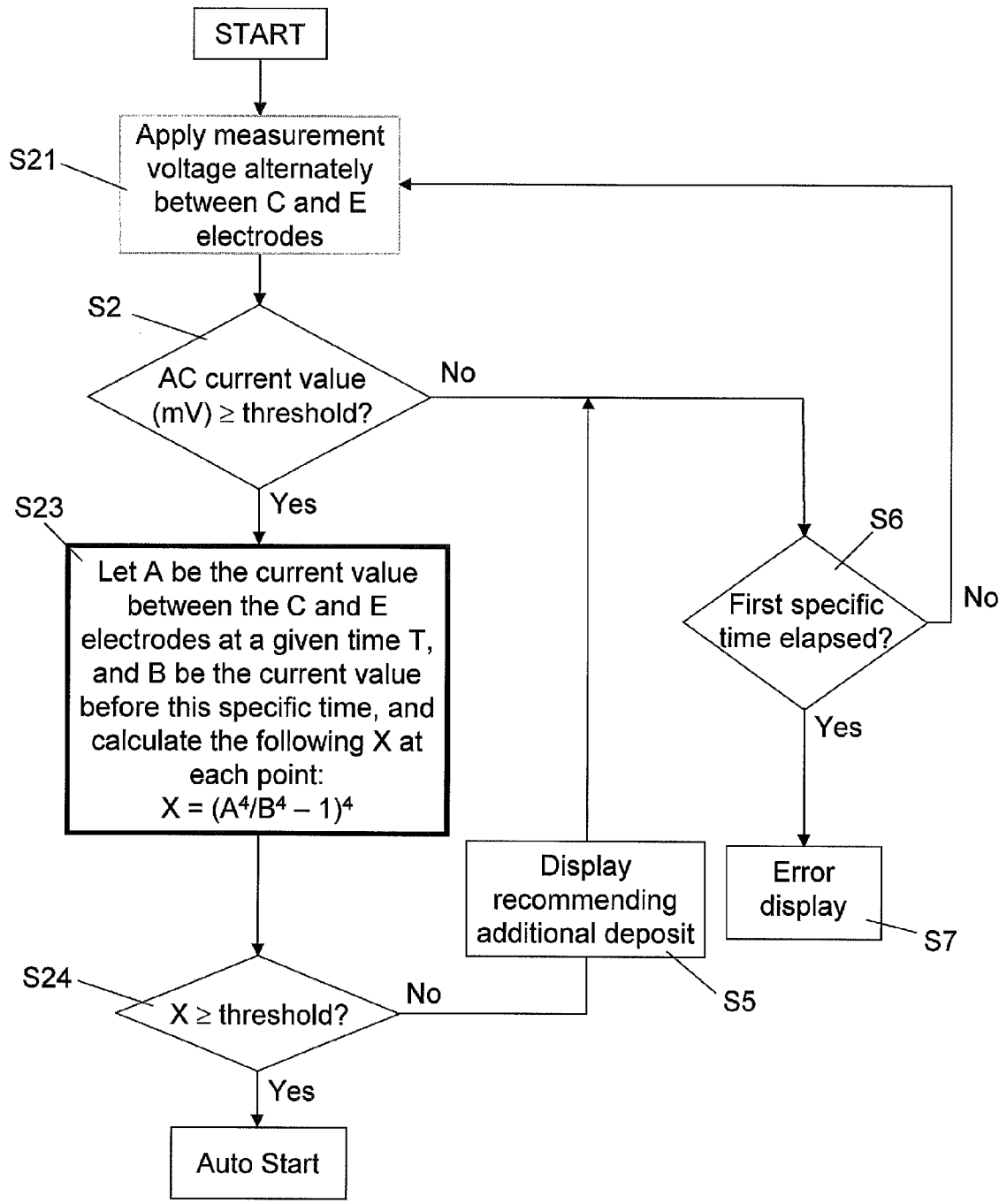
FIG. 9 is a flowchart of the flow in auto-start control by the biological sample measuring device pertaining to yet another embodiment of the present invention.

More specifically, as shown in step S21 in FIG. 9, the controller 20 determines whether the capillary is in a properly filled state or a state in which pass-around or seepage has occurred, on the basis of graphs (see FIGS. 10A and 10B) of the output result obtained by applying a specific voltage (preferably within a range of 150 mV to 1V, such as 500 mV) between the electrodes 8C and 8B (the C and E electrodes).

That is, in this embodiment, just as in Embodiment 1 above, we focus on the fact that there is a major difference in the proportional change in output current value versus elapsed time (the slope of the graph) between when a sufficient amount of biological sample was deposited (see FIG. 10A) and when an insufficient amount of biological sample was deposited and pass-around or seepage occurred (see FIG. 10B), and use a numerical value X that clearly represents this difference to compare with a specific threshold.

More specifically, as shown in step S23 in FIG. 9, if we let A be the output current value with respect to the voltage applied between the C and E electrodes at a given time T, and B be the output current value with respect to the voltage applied between the C and E electrodes before this first specific time (preferably within 0.01 to 2 seconds, such as 0.1 second), a value X is calculated on the basis of the following relational formula (3).

$$X = (A^4/B^4 - 1)^4 \quad (3)$$

Specifically, the value X here is calculated by subtracting "1" from the ratio of values of raising the output current values A and B to the fourth power, and then further raising this remainder to the fourth power.

In the above relational formula (3), the reason for raising the output current values A and B, etc., to the fourth power is the same as that with Relational Formula 1 in Embodiment 1 above, to improve the accuracy of threshold determination used to more accurately detect whether or not the capillary has been sufficiently filled with the biological sample.

In this embodiment, as shown in the flowchart in FIG. 9, first in step S21 a specific voltage (preferably within a range of 150 mV to 1 V, such as 500 mV) is applied between the C and E electrodes.

Step S2 is the same as in the flowchart in FIG. 5 in Embodiment 1 above.

Then, in step S23, the value X is calculated on the basis of the above-mentioned relational formula (3).

Next, in step S24, the value X calculated in step S23 is compared to a preset threshold. Here, when the value X is greater than or equal to the threshold, it is concluded that the capillary is filled with a sufficient amount of biological sample, and measurement voltage is applied to the electrodes 8A to 8C to start measurement automatically.

Figure 10A:
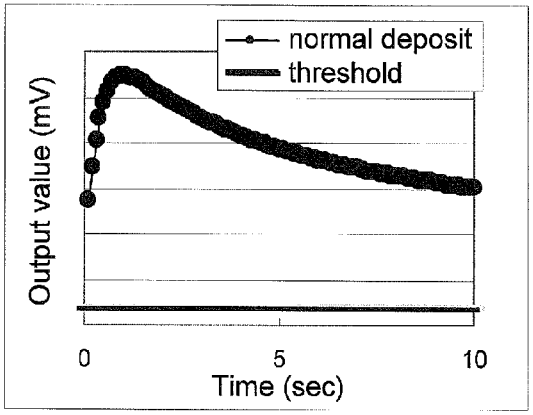
FIG. 10A is a graph of the output result versus elapsed time when just a normal amount of biological sample has been deposited on a sensor in the biological sample measuring device in yet another embodiment of the present invention.
Figure 10D:
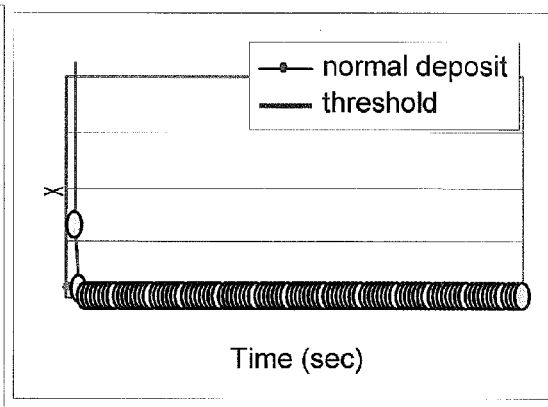
FIGS. 10D to 10F are graphs of the relation between the value of X and the elapsed time corresponding to FIGS. 10A to 10C.

More specifically, when a sufficient amount of biological sample has been deposited (with a normal deposit), as shown in FIG. 10D, the value X exceeds the threshold immediately after the application of voltage. Consequently, the controller 20 controls the voltage application section 12 so that voltage for starting measurement automatically will be applied. On the other hand, if an insufficient amount of biological sample has been deposited and pass-around or seepage has occurred, the value X will not exceed the threshold, as shown in FIG. 10E. Consequently, the controller 20 controls the voltage application section 12 so that no voltage is applied by mistake for starting measurement automatically.

The flow from step S5 and beyond is the same as in Embodiment 1 above, and therefore will not be described again here.

The threshold used during threshold determination in step S24 is preferably set according to the ambient temperature during measurement. As a specific example of this, when the ambient temperature T is below 20° C., the threshold is set to 0.3, when the ambient temperature T is at least 20° C. but below 30° C., the threshold is set to 1, and when the ambient temperature T is at least 30° C., the threshold is set to 2. The threshold is changed depending on the ambient temperature, and the degree of introduction of the biological sample is determined by comparison to the above-mentioned value X.

Consequently, even if the output current value changes due to a difference in the extent to which the reaction between the biological sample and the reagent 10 proceeds depending on how high or low the ambient temperature is, auto-start control can still be carried out very accurately regardless of changes in the ambient temperature.

A case was described here in which the temperature range (5 to 45 degrees) over which measurement is possible with the biological sample measuring device of this embodiment was divided in three, but the present invention is not limited to this. For example, the range may be divided in two or less, or may be divided more finely into four or more parts.

Figure 10B:
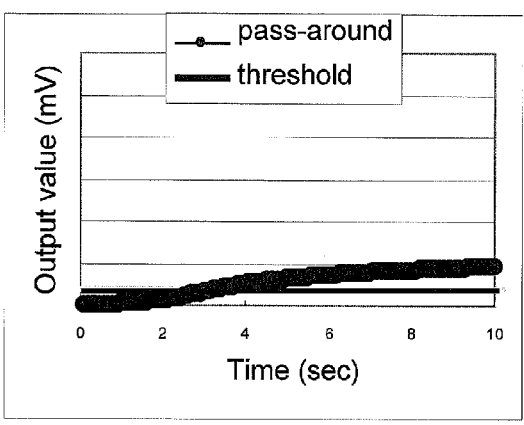
FIG. 10B is a graph of the output result versus elapsed time when there is not enough biological sample and pass-around or seepage has occurred.
Figure 10E:
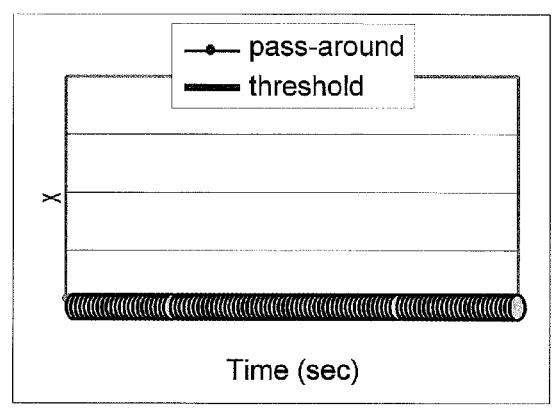
Figure 10C:
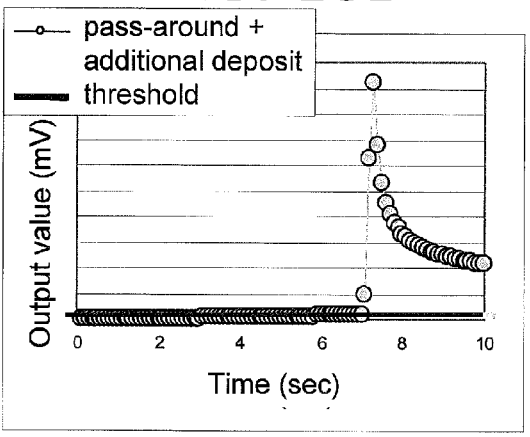
FIG. 10C is a graph of the output result versus elapsed time when an additional deposit has been made.

In step S5, if the patient makes an additional deposit of biological sample on the biological sample measuring sensor 3 because of a display recommending additional deposit, the capillary will be filled all at once with biological sample that will then react with the reagent 10, so as shown in FIG. 10C, the output current value rises sharply and appears as the peak current.

Figure 10F:
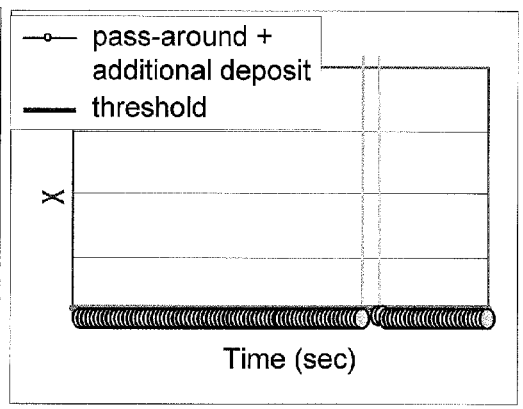

As shown in FIG. 10F, in this embodiment the filling state inside the capillary after additional deposit can be detected by detecting the peak current at which the value X calculated from the above-mentioned relational formula (3) exceeds the threshold. The threshold set for use in detecting the peak current may also be used in the detection of this peak current.

The thresholds in the graphs in FIGS. 10A and 10B are the ones used in conventional auto-start control.

That is, when auto-start control is carried out with this conventional threshold setting alone, then even though the capillary has not been sufficiently filled with biological sample, if the output current value obtained as a result of biological sample infiltrating to the ends of the capillary by pass-around or seepage and gradually reacting with the reagent 10 should end up being detected and exceeding the threshold, or if the output current value obtained as a result of the plasma component in blood reaching the detecting electrode while seeping into the reagent 10 and gradually reacting (after approximately 3 seconds have elapsed in FIG. 10B), measurement will end up being commenced automatically. If measurement is performed by applying measurement voltage to this insufficient amount of biological sample, there is the risk that the obtained measured value will be lower than the actual value.

With the biological sample measuring device of this embodiment, to accurately detect the degree of introduction of biological sample in the capillary, the value X is calculated from Relational Formula 3 on the basis of the numerical values A and B related to the slope of the graphs shown in FIGS. 10A and 10B, and threshold determination is performed by comparing the value X to a threshold, as shown in FIGS. 10D and 10E.

Consequently, whether or not the capillary has been sufficiently filled with the biological sample (the degree of introduction of the biological sample) can be detected more accurately by eliminating the effect of pass-around or seepage, than by conventional threshold determination in which the measurement result was simply compared to a threshold. As a result, measurement will not be automatically started until there is an additional deposit and the capillary is filled with a sufficient amount of biological sample, so more accurate auto-start control can be carried out.

Other Embodiments

Embodiments of the present invention were described above, but the present invention is not limited to or by the above embodiments, and various modifications are possible without departing from the gist of the invention.

(A)

In Embodiments 1, 2, and 3 above, an example was described in which the effect of pass-around or seepage was eliminated, and the position of the biological sample in the capillary was detected more accurately than in the past, by distinguishing between normal filling and when pass-around or seepage occurs, on the basis of the slope of the graphs indicating the output current value versus elapsed time when voltage was applied to the electrodes 8A, 8B, and 8C, etc. However, the present invention is not limited to this.

Figure 11A:
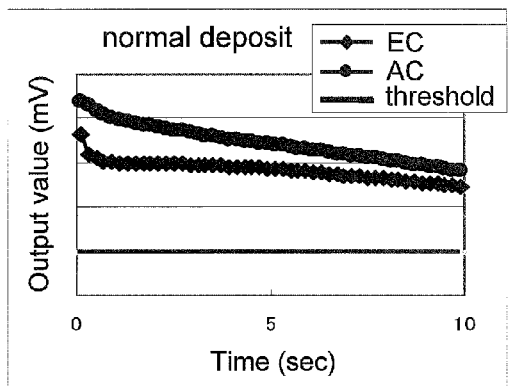
FIG. 11A is a graph of the output result versus elapsed time when just a normal amount of biological sample has been deposited on a sensor in the biological sample measuring device in another embodiment of the present invention.
Figure 11D:
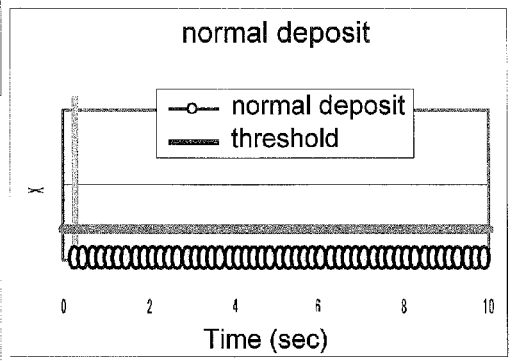
FIGS. 11D to 11F are graphs of the relation between the value of X and the elapsed time corresponding to FIGS. 11A to 11C.
Figure 11B:
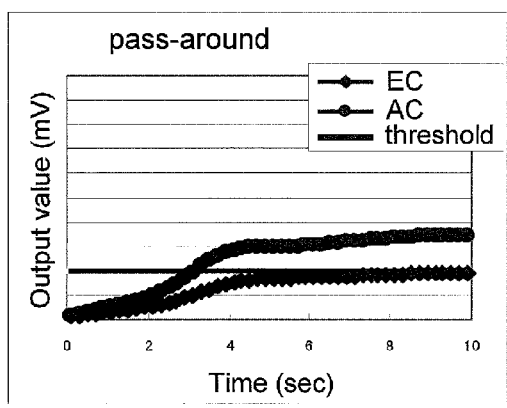
FIG. 11B is a graph of the output result versus elapsed time when there is not enough biological sample and pass-around or seepage has occurred.
Figure 11E:
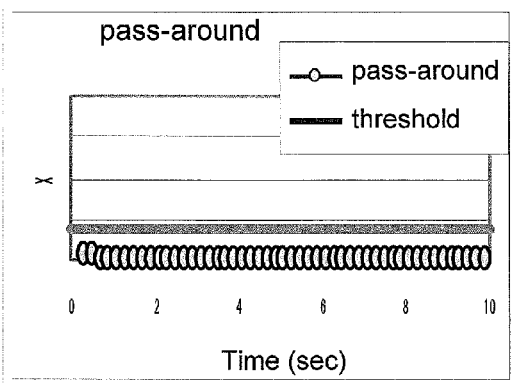
Figure 11C:
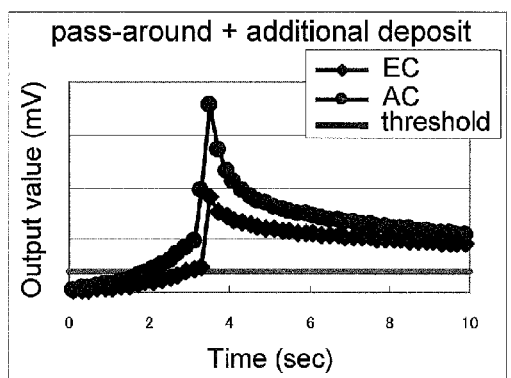
FIG. 11C is a graph of the output result versus elapsed time when an additional deposit has been made.
Figure 11F:
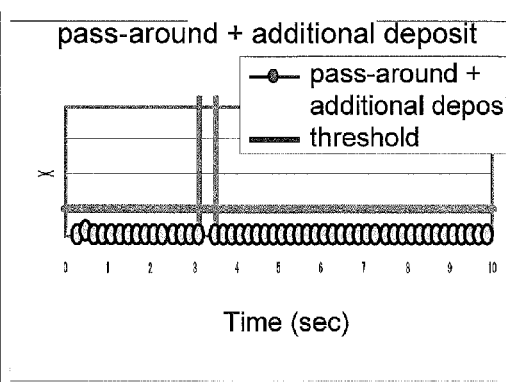

For example, threshold determination may be carried out by calculating the value X shown in FIGS. 11D to 11F on the basis of the graphs shown in FIGS. 11A to 11C, which show the output current value obtained at different elapsed times as a result of a specific voltage (preferably within a range of 150 mV to 1V, such as 500 mV) alternately between the E and C electrodes and between the A and C electrodes.

More specifically, if we let A be the output current value with respect to the voltage applied between the E and C electrodes at a given time T, and B be the output current value with respect to the voltage applied between the E and C electrodes before this first specific time (preferably within 0.01 to 2 seconds, such as 0.2 second), and if we let A' be the output current value with respect to the voltage applied between the A and C electrodes before a second specific time of the above-mentioned time T (preferably within 0.01 to 2 seconds, such as 0.1 second), and B' be the output current value with respect to the voltage applied between the A and C electrodes before this first specific time (preferably within 0.01 to 2 seconds, such as 0.2 second), a value X is calculated on the basis of the following relational formula (2).

$$X = (A \times A'/B \times B' - 1)^4 \qquad (2)$$

Just as in Embodiments 1 to 3 above, as shown in FIG. 11D, threshold determination is performed by comparing the X value with a threshold. If the value X and the threshold are compared and the X is found to exceed the threshold, the capillary is determined to be normally filled with biological sample, and measurement is started automatically. On the other hand, as shown in FIG. 11E, if X is below the threshold, it is determined that pass-around or seepage has occurred, and the system waits until an additional deposit (peak current value) is detected, as shown in FIGS. 11C and 11F.

Consequently, just as in Embodiments 1 to 3 above, whether or not the capillary has been sufficiently filled with the biological sample (the degree of introduction of the biological sample) can be detected more accurately by eliminating the effect of pass-around or seepage, than by conventional threshold determination in which the measurement result was simply compared to a threshold. As a result, measurement will not be automatically started until there is an additional deposit and the capillary is filled with a sufficient amount of biological sample, so more accurate auto-start control can be carried out.

(B)

In Embodiments 1, 2, and 3 above, an example was described in which the effect of pass-around or seepage was eliminated, and the position of the biological sample in the capillary was detected more accurately than in the past, by distinguishing between normal filling and when pass-around or seepage occurs, on the basis of the slope of the graphs indicating the output current value versus elapsed time when voltage was applied to the electrodes 8A, 8B, and 8C, etc. However, the present invention is not limited to this.

Figure 12A:
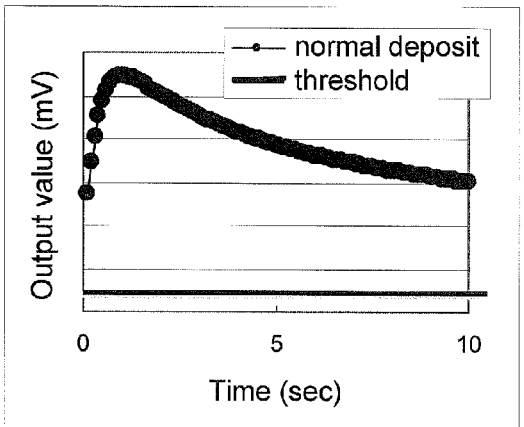
FIG. 12A is a graph of the output result versus elapsed time when just a normal amount of biological sample has been deposited on a sensor in the biological sample measuring device in another embodiment of the present invention.
Figure 12D:
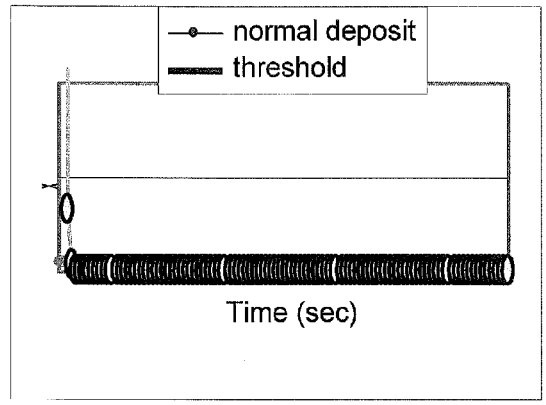
FIGS. 12D to 12F are graphs of the relation between the value of X and the elapsed time corresponding to FIGS. 12A to 12C.
Figure 12B:
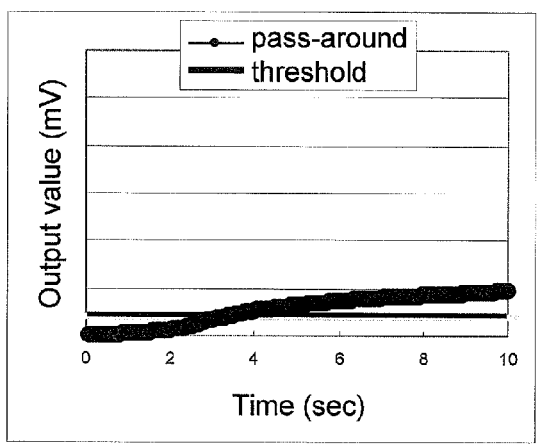
FIG. 12B is a graph of the output result versus elapsed time when there is not enough biological sample and pass-around or seepage has occurred.
Figure 12E:
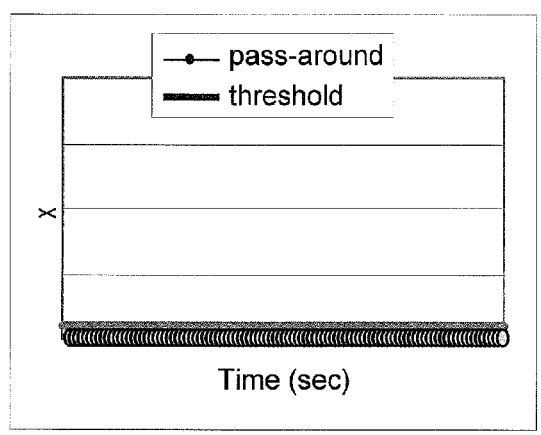

For example, threshold determination may be carried out by calculating the value X shown in FIGS. 12D and 12E by taking advantage of the fact that there is a clear difference in the curves of the graph during a normal deposit (see FIG. 12A), which shows the output current value obtained at various elapsed times when a specific voltage (preferably within a range of 150 mV to 1 V, such as 500 mV) was applied between the A and C electrodes, and of the graph when pass-around or seepage has occurred (see FIG. 12B), just as in Embodiment 1 above.

More specifically, if we let A be the output current value at a given time T, B be the output current value before this specific time (preferably within 0.01 to 2 seconds, such as 0.1 second), A' be the output current value before the specific time of A (preferably within 0.01 to 2 seconds, such as 0.5 second), and B' be the output current value before the specific time of B (preferably within 0.01 to 2 seconds, such as 0.5 second), a value X is calculated on the basis of the following relational formula (4).

$$X = (A - B) \div (A' - B') \qquad (4)$$

Figure 12C:
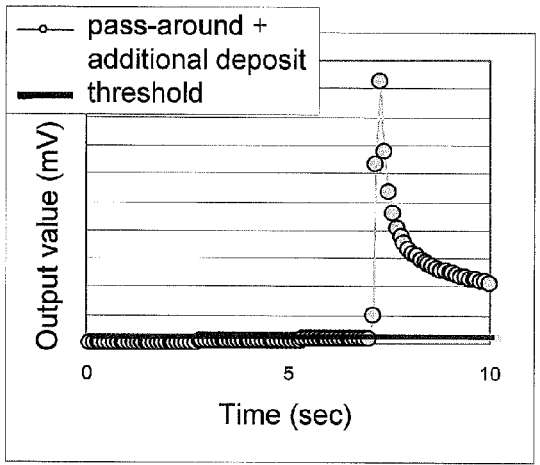
FIG. 12C is a graph of the output result versus elapsed time when an additional deposit has been made.
Figure 12F:
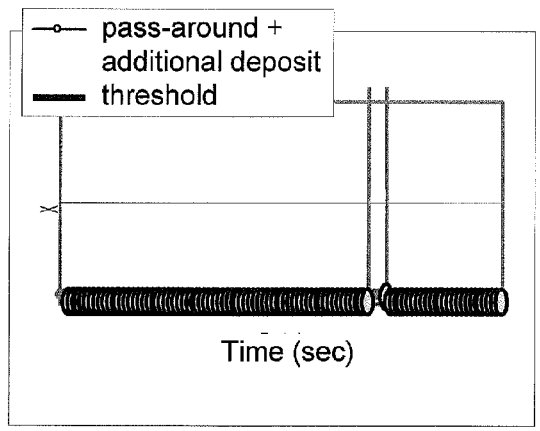

Just as in Embodiments 1 to 3 above, as shown in FIGS. 12D and 12E, when the calculated value X is compared to a specific threshold, and X is found to exceed the threshold, it is determined that the capillary has been normally filled with biological sample, and measurement is started automatically. On the other hand, if X is below the threshold, it is determined that pass-around or seepage has occurred, and the system waits until an additional deposit (peak current value) is detected, as shown in FIGS. 12C and 12F.

In this case, the threshold may be set to "5," for example.

Consequently, just as in Embodiments 1 to 3 above, whether or not the capillary has been sufficiently filled with the biological sample (the degree of introduction of the biological sample) can be detected more accurately by eliminating the effect of pass-around or seepage, than by conventional threshold determination in which the measurement result was simply compared to a threshold. As a result, measurement will not be automatically started until there is an additional deposit and the capillary is filled with a sufficient amount of biological sample, so more accurate auto-start control can be carried out.

(C)

In Embodiments 1, 2, and 3 above, an example was described in which the effect of pass-around or seepage was eliminated, and the position of the biological sample in the capillary was detected more accurately than in the past, by distinguishing between normal filling and when pass-around or seepage occurs, on the basis of the slope of the graphs indicating the output current value versus elapsed time when voltage was applied to the electrodes 8A, 8B, and 8C, etc. However, the present invention is not limited to this.

Figure 13A:
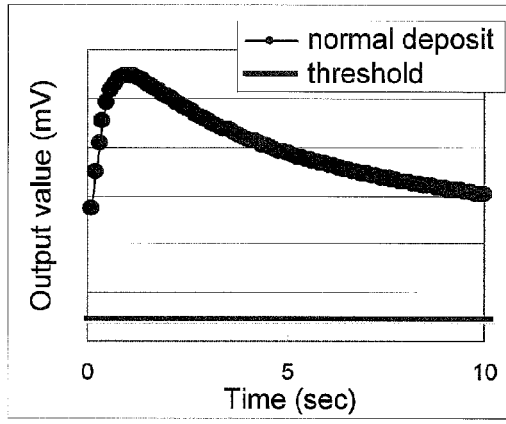
FIG. 13A is a graph of the output result versus elapsed time when just a normal amount of biological sample has been deposited on a sensor in the biological sample measuring device in another embodiment of the present invention.
Figure 13D:
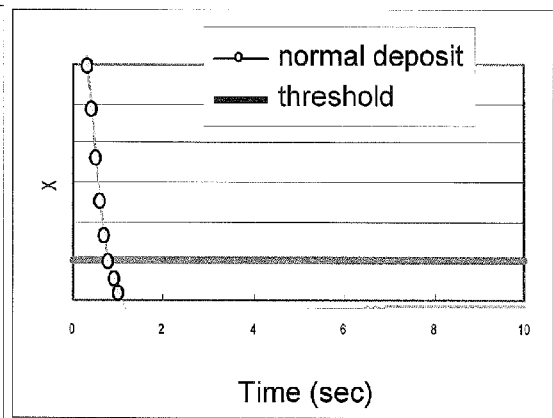
FIGS. 13D to 13F are graphs of the relation between the value of X and the elapsed time corresponding to FIGS. 13A to 13C.
Figure 13B:
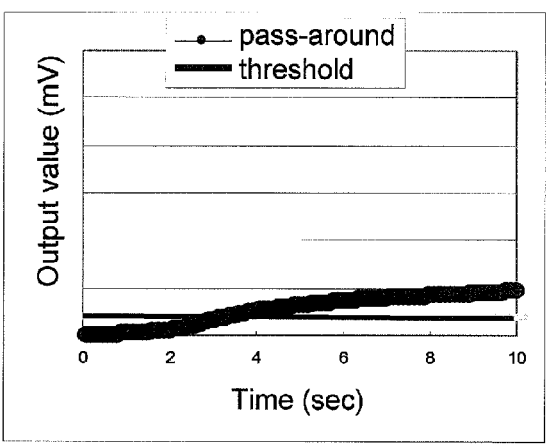
FIG. 13B is a graph of the output result versus elapsed time when there is not enough biological sample and pass-around or seepage has occurred.
Figure 13E:
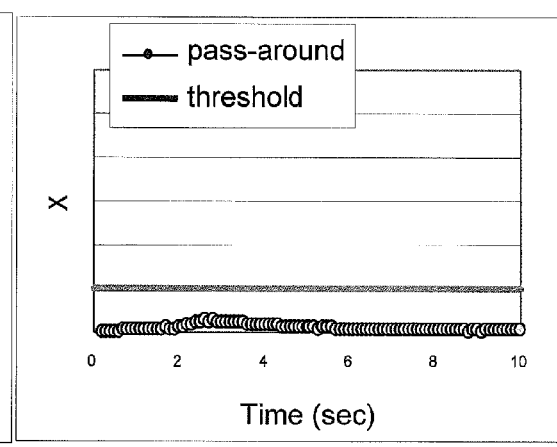
Figure 13C:
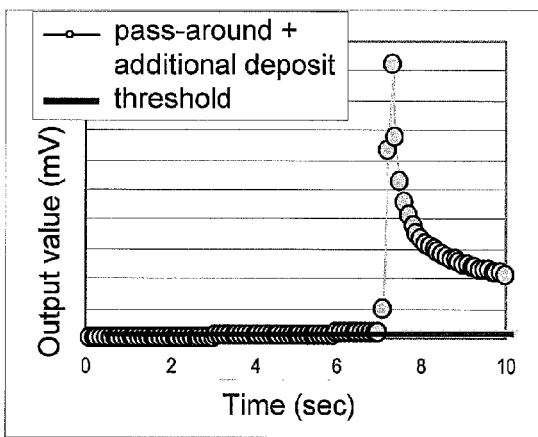
FIG. 13C is a graph of the output result versus elapsed time when an additional deposit has been made.

For example, threshold determination may be carried out by calculating the value X shown in FIGS. 13D and 13E on the basis of the graphs shown in FIGS. 13A to 13C, which shown the output current value obtained at various elapsed times when a specific voltage (such as 500 mV) was applied between the A and C electrodes, just as in Embodiment 1 above.

More specifically, the slope of the graph may be calculated by taking advantage of the fact that there is a clear difference in the curves of the graph during a normal deposit (see FIG. 13A) and of the graph when pass-around or seepage has occurred (see FIG. 13B), and taking two points at the front and rear of the waveform of the graph, and using the result as the value X.

Figure 13F:
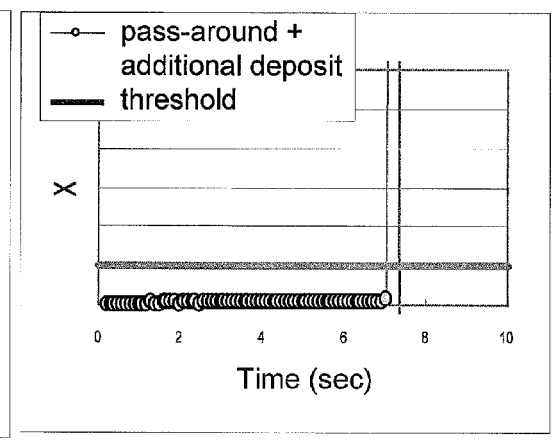

Just as in Embodiments 1 to 3 above, as shown in FIGS. 13D and 13E, when the calculated value X is compared to a specific threshold, and X is found to exceed the threshold, it is determined that the capillary has been normally filled with biological sample, and measurement is started automatically. On the other hand, if X is below the threshold, it is determined that pass-around or seepage has occurred, and the system waits until an additional deposit (peak current value) is detected, as shown in FIGS. 13C and 13F.

In this case, the threshold may be set to "50," for example.

Consequently, just as in Embodiments 1 to 3 above, whether or not the capillary has been sufficiently filled with the biological sample (the degree of introduction of the biological sample) can be detected more accurately by eliminating the effect of pass-around or seepage, than by conventional threshold determination in which the measurement result was simply compared to a threshold. As a result, measurement will not be automatically started until there is an additional deposit and the capillary is filled with a sufficient amount of biological sample, so more accurate auto-start control can be carried out.

(D)

In the above embodiments, an example was described in which the value X used in threshold determination was calculated by raising the values of output current, etc., to the fourth power in order to improve the accuracy of threshold determination in step S3 shown in FIG. 5. However, the present invention is not limited to this.

How the value X is calculated is not limited to raising to the fourth power, and may instead be, for example, to improve the accuracy of threshold determination by setting the value of n and raising a value to the n-th power in a function using the numerical values A, B, etc., so that the calculation accuracy of these output values will be increased the most.

(E)

In Embodiment 1 above, an example was described in which the electrode 8A (second electrode), the electrode 8B (third electrode), and the electrode 8C (first electrode) were provided on the top face of the substrate 5. However, the present invention is not limited to this.

Figure 14A:
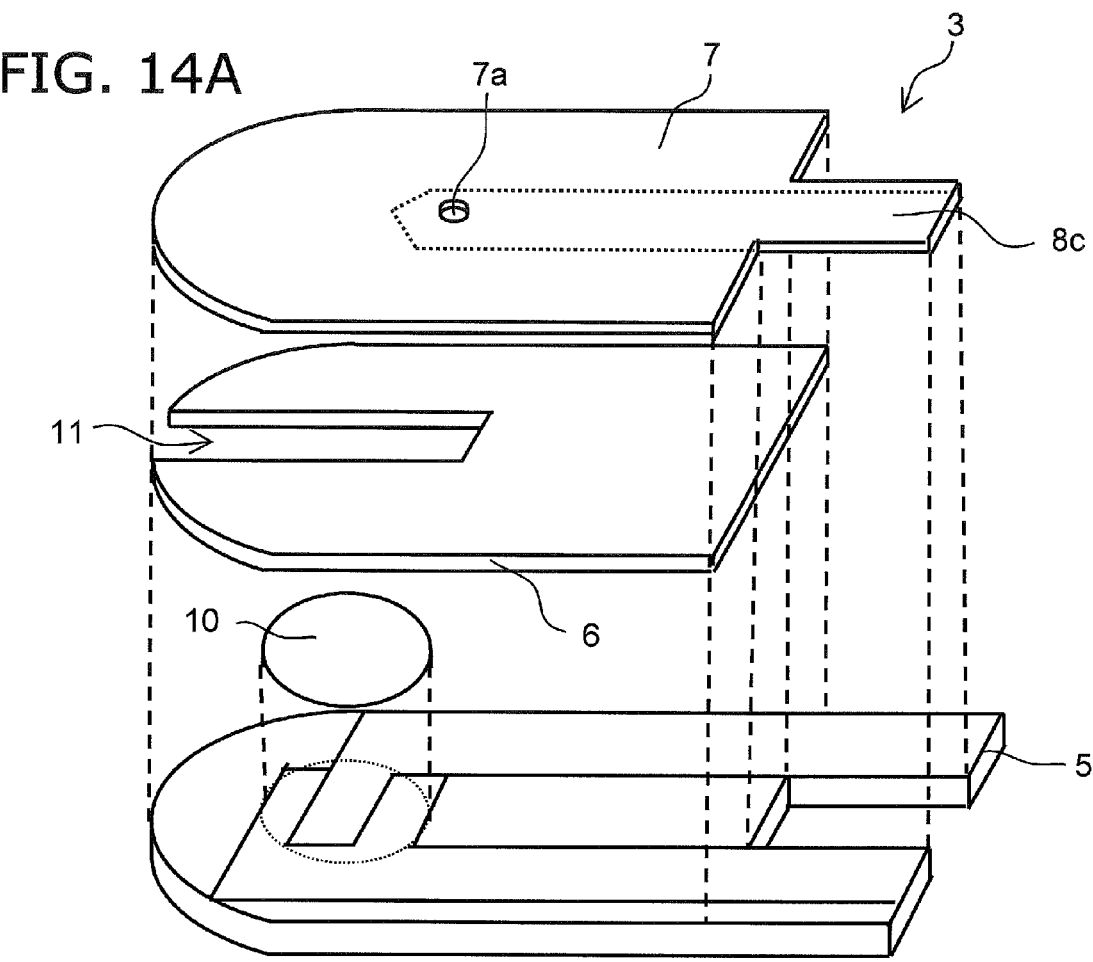
FIG. 14A is an exploded oblique view of the biological sample measuring sensor used in the biological sample measuring device in yet another embodiment of the present invention.
Figure 14B:
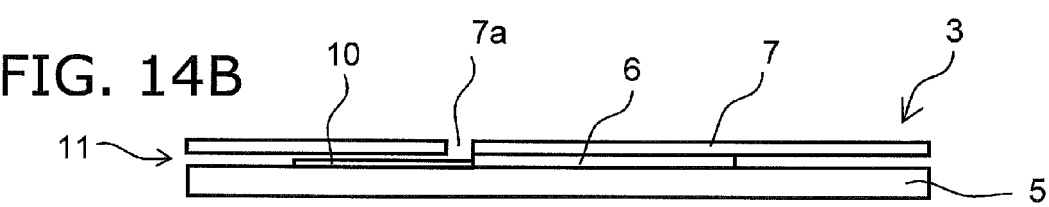
FIG. 14B is a side cross section thereof.
Figure 14C:
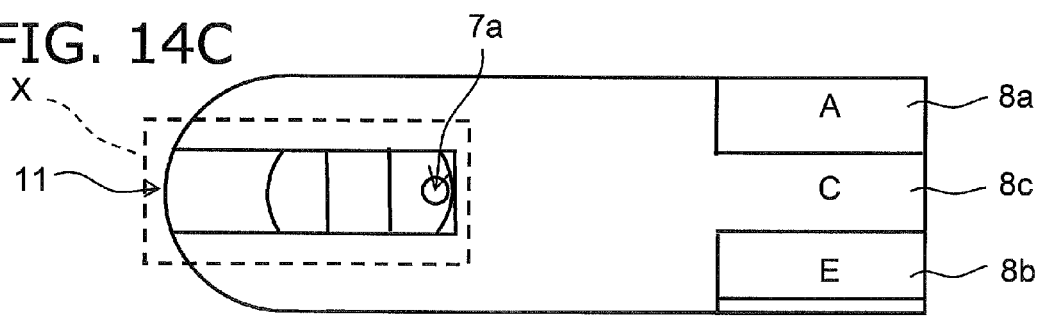
FIG. 14C is a plan view thereof.
Figure 15:
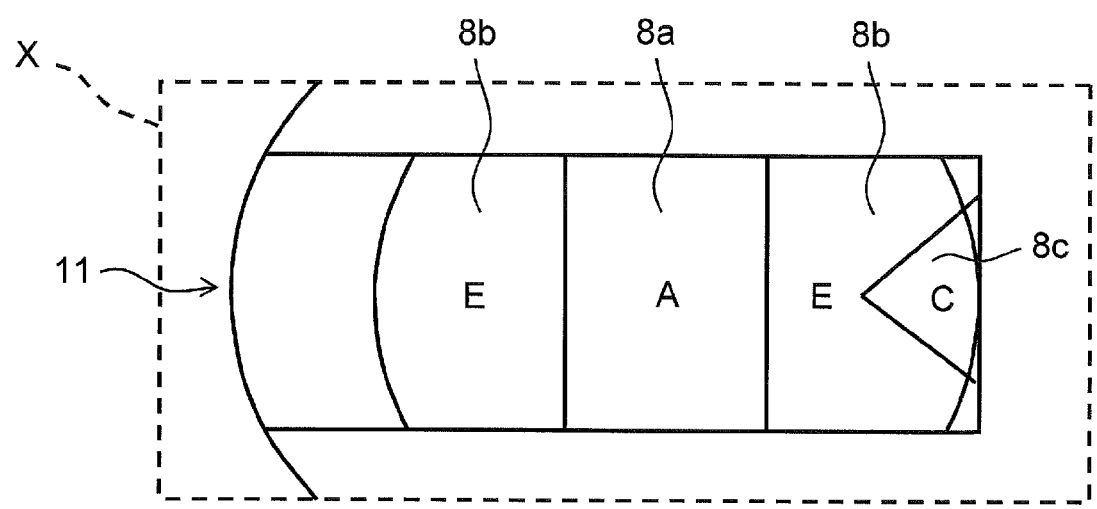
FIG. 15 is a detail view of the X portion of the biological sample measuring sensor in FIG. 14C.

For example, as shown in FIGS. 14A to 14C, instead of providing the electrode 8C (first electrode) on the adhesion side of the substrate 5, it may be provided near the approximate center on the adhesion side of the cover 7.

In this case, it must be provided inside the mounting portion 4 on the biological sample measuring device side, and provided with the orientation reversed on the contact terminal in contact with the electrode 8C provided on the adhesion side of the cover 7. Also, the terminals in contact with the electrodes 8A and 8B provided on the substrate 5 side are in contact facing downward from above, while the terminal in contact with the electrode 8C provided on the cover 7 side is in contact facing upward from below.

Thus, cut-outs are provided as shown in FIG. 14A to the portion of the substrate 5 opposite the electrode 8C provided on the cover 7 side and to the portion of the cover 7 opposite the electrodes 8A and 8B provided on the substrate 5 side, ensuring enough space for the connection terminals on the device side to fit in.

Also, even with the above electrode layout, the electrode 8C provided on the cover 7 side is provided at the deepest part of the capillary, just as with the electrode layout in Embodiment 1. Consequently, even if there is too little biological sample deposited on the biological sample measuring sensor, and the capillary is not sufficiently filled with the biological sample, this will prevent misdetection of the biological sample due to pass-around or seepage, and the position to which the biological sample fills the capillary can be accurately detected, which is the same effect as that achieved with the configuration in Embodiment 1.

(F)

In the above embodiments, an example was described in which the electrode 8A (second electrode), the electrode 8B (third electrode), and the electrode 8C (first electrode) were provided on the top face of the substrate 5. However, the present invention is not limited to this.

Figure 16A:
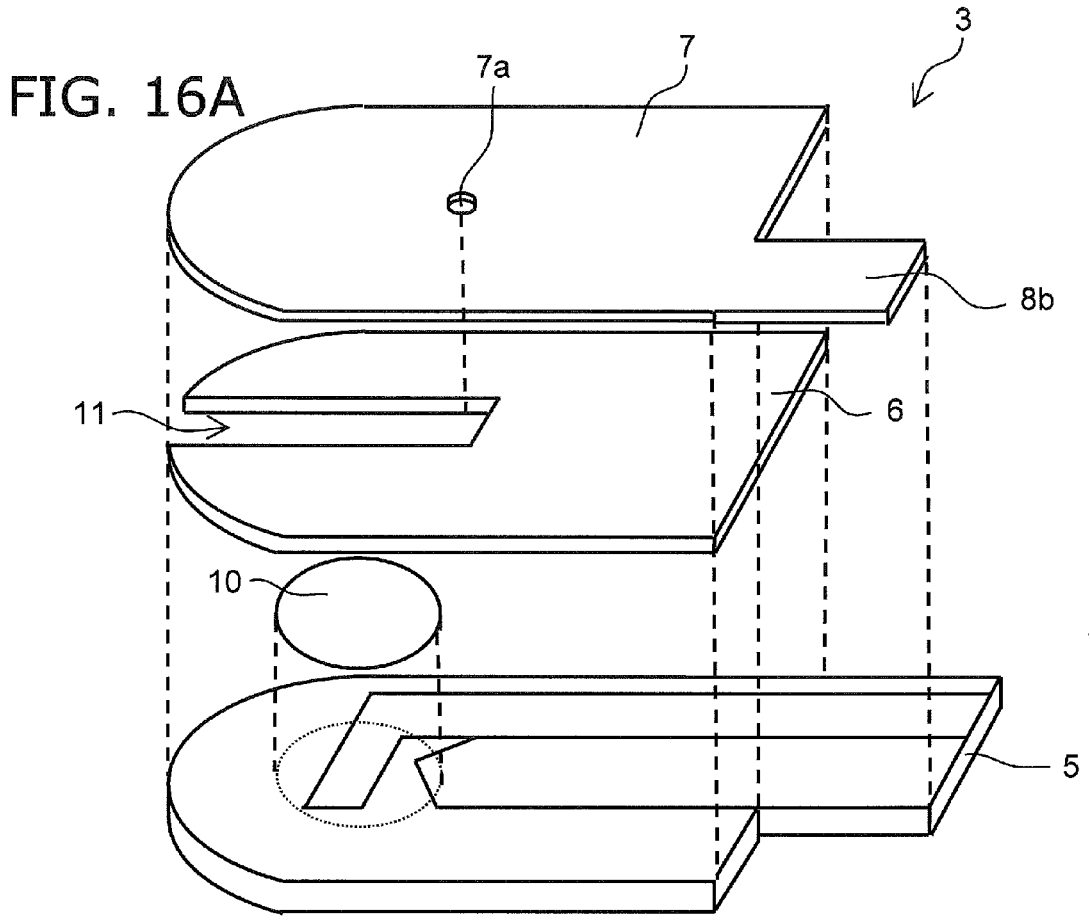
FIG. 16A is an exploded oblique view of the biological sample measuring sensor used in the biological sample measuring device in yet another embodiment of the present invention.
Figure 16B:
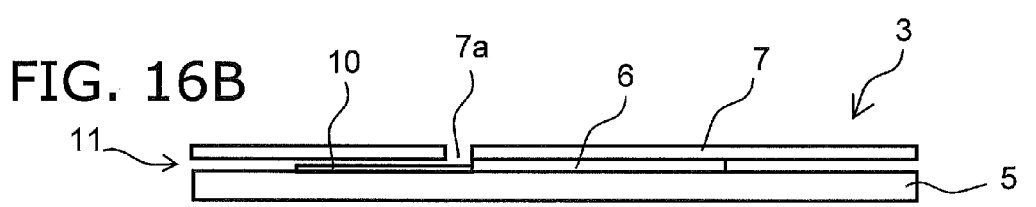
FIG. 16B is a side cross section thereof.
Figure 16C:
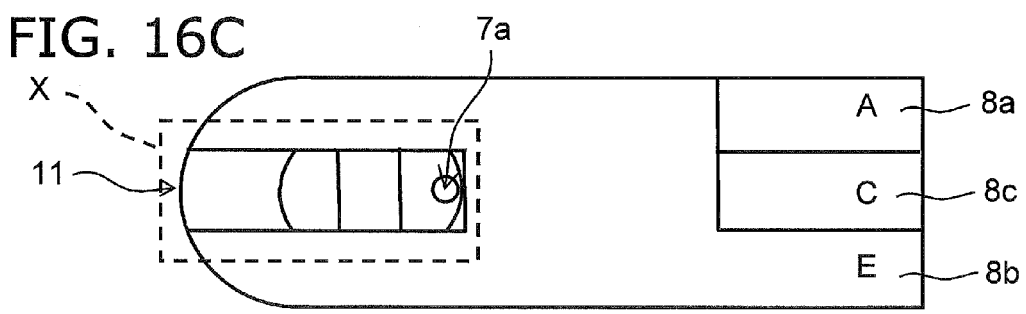
FIG. 16C is a plan view thereof.
Figure 17:
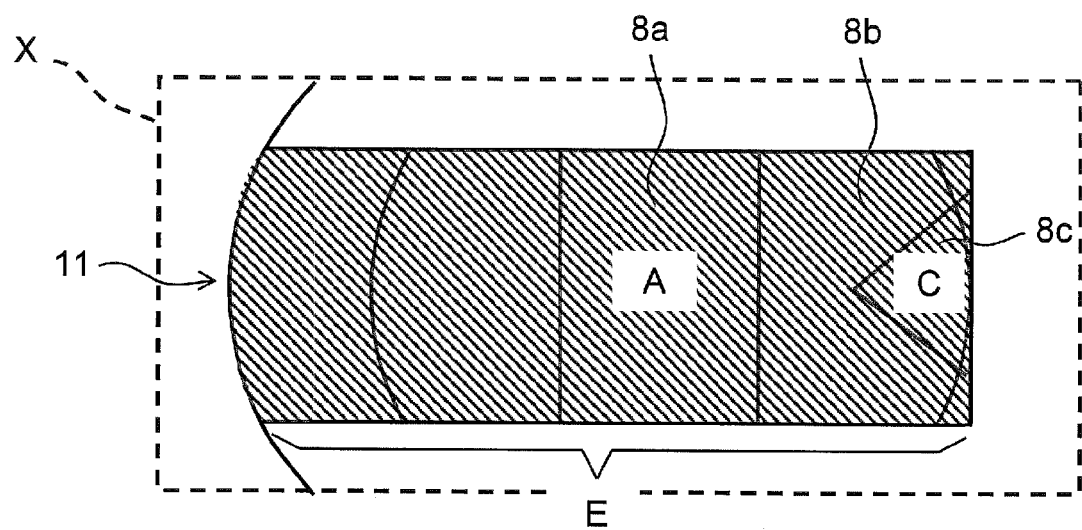
FIG. 17 is a detail view of the X portion of the biological sample measuring sensor in FIG. 16C.

For example, as shown in FIGS. 16A to 16C, instead of providing the electrode 8B (third electrode) to the adhesion side of the substrate 5, it may be provided over substantially the entire surface on the adhesion side of the cover 7.

In this case, it must be provided inside the mounting portion 4 on the biological sample measuring device side, and provided with the orientation reversed on the contact terminal in contact with the electrode 8B provided on the adhesion side of the cover 7. Also, the terminals in contact with the electrodes 8A and 8C provided on the substrate 5 side are in contact facing downward from above, while the terminal in contact with the electrode 8B provided on the cover 7 side is in contact facing upward from below.

Thus, cut-outs are provided as shown in FIG. 16A to the portion of the substrate 5 opposite the electrode 8B provided on the cover 7 side and to the portion of the cover 7 opposite the electrodes 8A and 8C provided on the substrate 5 side, ensuring enough space for the connection terminals on the device side to fit in.

Also, even with the above electrode layout, the electrode 8B provided on the cover 7 side is provided at the deepest part of the capillary, just as with the electrode layout in Embodiment 1. Consequently, even if there is too little biological sample deposited on the biological sample measuring sensor, and the capillary is not sufficiently filled with the biological sample, this will prevent misdetection of the biological sample due to pass-around or seepage, and the position to which the biological sample fills the capillary can be accurately detected, which is the same effect as that achieved with the configuration in Embodiment 1.

(G)

In the above embodiments, an example was described in which the capillary was formed in the lengthwise direction of the biological sample measuring sensor 3, and blood or another such biological sample was deposited from the end in the lengthwise direction of the biological sample measuring sensor 3. However, the present invention is not limited to this.

Figure 18A:
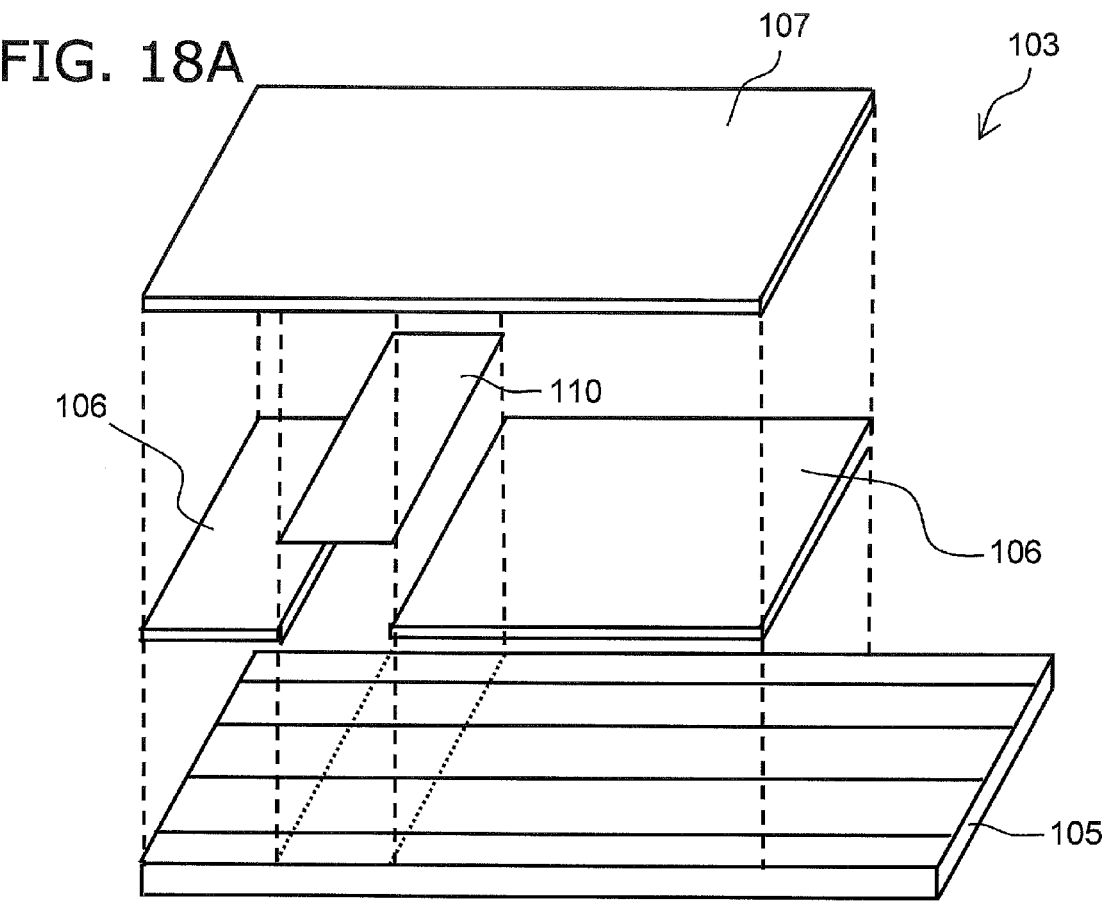
FIG. 18A is an exploded oblique view of the biological sample measuring sensor used in the biological sample measuring device in yet another embodiment of the present invention.
Figure 18B:
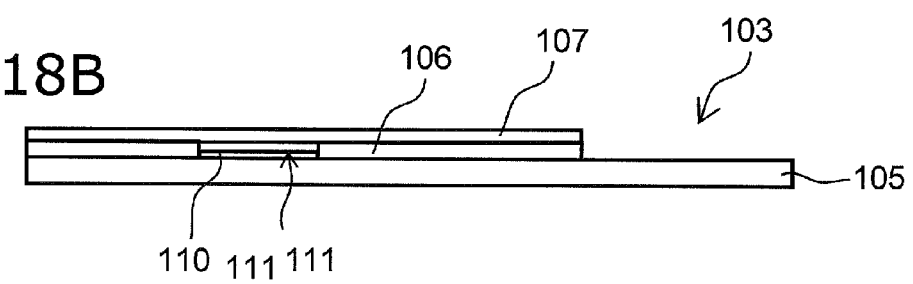
FIG. 18B is a side cross section thereof.
Figure 18C:
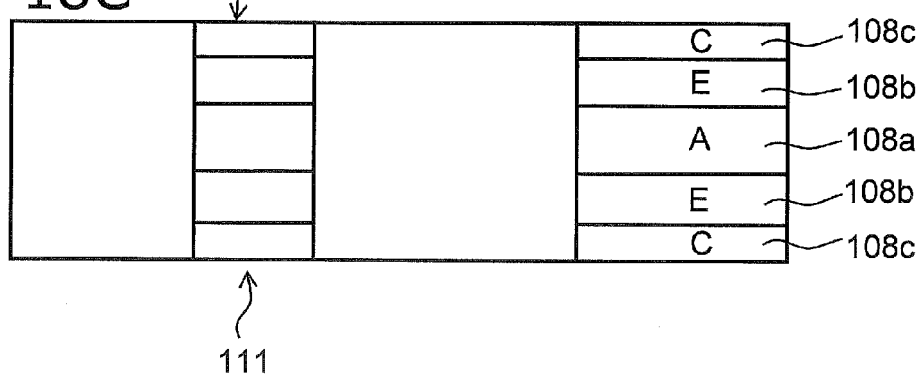
FIG. 18C is a plan view thereof.

For example, as shown in FIGS. 18A to 18C, a biological sample measuring sensor 103 may be configured so that the capillary is formed in a direction perpendicular to the lengthwise direction, allowing the biological sample to be deposited from both sides on the side face.

In this case, the capillary is formed in the width direction by two spacers 106 that are sandwiched between a substrate 105 and a cover 107, and a reagent 110 is provided along the capillary. With the biological sample measuring sensor 103, an electrode 108A (second electrode) is provided in the approximate center of the substrate 105, electrodes 108B (third electrodes) are provided on both sides of the electrode 108A, and electrodes 108C (first electrodes) are provided on the outside of the electrodes 108B.

Consequently, the side on which the output value of a specific threshold (current or voltage) is obtained can be detected as the side where the biological sample is supplied by applying a specific voltage alternately at specific time intervals between the two upper electrodes 108B and 108C and the two lower electrodes 108B and 108C shown in FIG. 18C. After the side where the biological sample is supplied has been detected, the measurement of the biological sample can be carried out by utilizing the electrode 108C disposed deeper with respect to the direction in which the biological sample flows in, of the two electrodes 8C.

Also, with the above electrode layout, if the above processing is carried out in the same manner, even if too little of the biological sample has been deposited on the biological sample measuring sensor and the capillary is not sufficiently filled with biological sample, misdetection of the biological sample due to pass-around or seepage will be prevented, and the position to which the biological sample fills the capillary can be accurately detected, which is the same effect as that achieved with the configuration in Embodiment 1.

INDUSTRIAL APPLICABILITY

The effect of the biological sample measuring device of the present invention is that the degree of introduction of a biological sample in the capillary of a sensor can be accurately detected, without being affected by pass-around or seepage, even if there is too little biological sample deposited on the sensor, so this technology can be widely applied to biological sample measuring devices that measure biological information such as blood glucose levels.

General Interpretation of Terms

In understanding the scope of the present disclosure, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Also, the terms "part," "section," "portion," "member" or "element" when used in the singular can have the dual meaning of a single part or a plurality of parts. Also as used herein to describe the above embodiment(s), the following directional terms "forward", "rearward", "above", "downward", "vertical", "horizontal", "below" and "transverse" as well as any other similar directional terms refer to those directions of the biological sample measuring device. Accordingly, these terms, as utilized to describe the technology disclosed herein should be interpreted relative to the biological sample measuring device.

The term "configured" as used herein to describe a component, section, or part of a device includes hardware and/or software that is constructed and/or programmed to carry out the desired function.

The terms of degree such as "substantially", "about" and "approximately" as used herein mean a reasonable amount of deviation of the modified term such that the end result is not significantly changed.

While only selected embodiments have been chosen to illustrate the present invention, it will be apparent to those skilled in the art from this disclosure that various changes and modifications can be made herein without departing from the scope of the invention as defined in the appended claims. For example, the size, shape, location or orientation of the various components can be changed as needed and/or desired. Components that are shown directly connected or contacting each other can have intermediate structures disposed between them. The functions of one element can be performed by two, and vice versa. The structures and functions of one embodiment can be adopted in another embodiment. It is not necessary for all advantages to be present in a particular embodiment at the same time. Every feature which is unique from the prior art, alone or in combination with other features, also should be considered a separate description of further inventions by the applicants, including the structural and/or functional concepts embodied by such feature(s). Thus, the foregoing descriptions of the embodiments according to the present invention are provided for illustration only, and not for the purpose of limiting the invention as defined by the appended claims and their equivalents.

The invention claimed is:

1. A biological sample measuring device comprising:
a mounting portion;
a voltage application section configured to apply a voltage to a plurality of electrodes; and
a controller configured to:
determine an output result based on applying the voltage of the voltage application section to the electrodes,
detect a degree to which a biological sample is introduced into a capillary based on the output result, and
eliminate misdetection of the biological sample due to seepage or pass-around.

2. The biological sample measuring device according to claim 1, wherein:
the controller is further configured to:
detect an additional deposit of the biological sample,
determine that the capillary contains an insufficient quantity of the biological sample based on the degree to which the biological sample is introduced into the capillary, and
detect that the output result has exceeded a specific threshold after the controller has determined that the capillary contains an insufficient quantity of the biological sample.

3. The biological sample measuring device according to claim 1, wherein:
the electrodes include:
a first electrode disposed inside the capillary, and
a second electrode disposed closer to an inlet of the capillary than the first electrode in a region of the capillary where a reagent is provided;
the output result is determined based on applying the voltage between the first electrode and the second electrode; and
the controller is further configured to determine whether the capillary is in a properly filled state, or in a state in which pass-around or seepage has occurred, based on a function related to the output result.

4. The biological sample measuring device according to claim 1, wherein:
the electrodes include:
a first electrode disposed inside the capillary,
a second electrode disposed closer to an inlet of the capillary than the first electrode in a region of the capillary where a reagent is provided, and
a third electrode that is including:
a first portion of the third electrode disposed closer to the inlet of the capillary than the second electrode, and
a second portion of the third electrode disposed between the first and second electrodes;
the output result determined based on alternately applying the voltage between:
the first electrode and the third electrode, and
the first electrode and the second electrode,
the voltage applied for a predetermined length of time to each pair of electrodes; and
the controller is further configured to determine whether the capillary is in a properly filled state, or in a state in which pass-around or seepage has occurred, based on a function related the output result.

5. The biological sample measuring device according to claim 1, wherein:
the electrodes include:
a first electrode disposed inside the capillary,
a second electrode disposed closer to an inlet of the capillary than the first electrode in a region of the capillary where a reagent is provided, and
a third electrode including:
a first portion of the third electrode disposed closer to the inlet of the capillary than the second electrode, and
a second portion of the third electrode disposed between the first and second electrodes;
the output result is determined based on applying the voltage between the first electrode and the third electrode; and
the controller is further configured to determine whether the capillary is in a properly filled state, or in a state in which pass-around or seepage has occurred, based on a function related to the output result.

6. The biological sample measuring device according to claim 1, further comprising:
a display section configured to display information related to the biological sample; and wherein the controller is further configured to:
  determine a detection result based on the degree to which the biological sample is introduced into the capillary, and
  display, on the display section, an indication recommending an additional deposit of the biological sample based on the detection result.

7. The biological sample measuring device according to claim 1, further comprising:
  a display section configured to display information related to the biological sample,
  wherein the controller is further configured to:
    determine a detection result based on the degree to which the biological sample is introduced into the capillary, and
    display, on the display section, an indication of a measurement error based on the detection result.

8. The biological sample measuring device according to claim 1, further comprising:
  a biological sample measuring sensor including the capillary;
  wherein the biological sample measuring sensor is configured to be removably mounted to the mounting portion.

9. The biological sample measuring device according to claim 1, wherein:
  the electrodes include:
    a first electrode including a first portion disposed inside the capillary,
    a second electrode disposed closer to an inlet of the capillary than the first electrode in a region of the capillary where the reagent is provided, and
    a third electrode including a first portion disposed closer to the inlet of the capillary than the second electrode; and
  the controller is further configured to determine whether the capillary is in a properly filled state, or in a state in which pass-around or seepage has occurred, based on a function related to the output result.

10. The biological sample measuring device according to claim 9, wherein:
  the output result is determined based on applying the voltage between the first electrode and the second electrode.

11. The biological sample measuring device according to claim 9, wherein:
  the output result is determined based on alternately applying the voltage between:
    the first electrode and the third electrode, and
    the first electrode and the second electrode.

12. The biological sample measuring device according to claim 9, wherein:
  the third electrode further includes a second portion disposed between the first and second electrodes.

13. The biological sample measuring device according to claim 12, wherein:
  the output result is determined based on applying the voltage between the first electrode and the third electrode.

14. The biological sample measuring device according to claim 12, wherein:
  the output result is determined based on alternately applying the voltage between:
    the first electrode and the third electrode, and
    the first electrode and the second electrode.

15. The biological sample measuring device according to claim 12, wherein:
  the first electrode further includes a second portion disposed closer to the inlet of the capillary than the first portion of the third electrode.

16. The biological sample measuring device according to claim 15, wherein:
  the output result is determined based on alternately applying the voltage between:
    the first portion of the first electrode and the second portion of the third electrode, and
    the second portion of the first electrode and the first portion of the third electrode.

* * * * *